(12) United States Patent
Yeung

(10) Patent No.: US 11,903,561 B2
(45) Date of Patent: Feb. 20, 2024

(54) SURGICAL SYSTEMS AND DEVICES, AND METHODS FOR CONFIGURING SURGICAL SYSTEMS AND PERFORMING ENDOSCOPIC PROCEDURES, INCLUDING ERCP PROCEDURES

(71) Applicant: Chung Kwong Yeung, Hong Kong (CN)

(72) Inventor: Chung Kwong Yeung, Hong Kong (CN)

(73) Assignee: IEMIS (HK) Limited, Kowloon (HK)

( * ) Notice: Subject to any disclaimer, the term of this patent is extended or adjusted under 35 U.S.C. 154(b) by 128 days.

(21) Appl. No.: 17/306,726

(22) Filed: May 3, 2021

(65) Prior Publication Data
US 2022/0346637 A1 Nov. 3, 2022

(51) Int. Cl.
*A61B 1/018* (2006.01)
*A61B 1/05* (2006.01)
*A61B 1/00* (2006.01)

(52) U.S. Cl.
CPC .......... *A61B 1/018* (2013.01); *A61B 1/00045* (2013.01); *A61B 1/000096* (2022.02);
(Continued)

(58) Field of Classification Search
CPC ... A61B 1/018; A61B 1/0125; A61B 1/00097; A61B 1/000096; A61B 1/00045; A61B 1/05; A61B 1/00087; A61B 1/00098; A61B 2562/0219; A61B 2034/2048; A61B 2034/301–304; A61B 34/30
See application file for complete search history.

(56) References Cited

U.S. PATENT DOCUMENTS 9,204,939 B2 * 12/2015 Frimer ............... A61B 1/00006
9,955,986 B2 * 5/2018 Shah ....................... A61B 34/71
(Continued)

FOREIGN PATENT DOCUMENTS

WO  WO-2022076790 A1 * 4/2022

OTHER PUBLICATIONS

Y. He, P. Zhang, X. Qi, B. Zhao, S. Li and Y. Hu, "Endoscopic Path Planning in Robot-Assisted Endoscopic Nasal Surgery," in IEEE Access, vol. 8, pp. 17039-17048, 2020, doi: 10.1109/ACCESS.2020.2967474.*

(Continued)

*Primary Examiner* — Ryan N Henderson
(74) *Attorney, Agent, or Firm* — Baker & McKenzie LLP

(57) ABSTRACT

Embodiments relate to surgical systems and methods. The system includes a main assembly having an IMU subsystem, camera, scope head assembly, and processor. Processor processes images and IMU information, including determining whether images include a distal end of the scope head assembly and a cannulation target. Responsive to a determination that images include the distal end of the scope head assembly, the processor generates 3-dimensional position of distal end of the scope head assembly. When images are determined to include the cannulation target, the processor generates 3-dimensional positions of the cannulation target. Processor also generates predictions of one or more real-time trajectory paths for the distal end of the scope head assembly to cannulate the cannulation target.

9 Claims, 9 Drawing Sheets

(52) U.S. Cl.
CPC ............ *A61B 1/00097* (2022.02); *A61B 1/05* (2013.01); *A61B 2562/0219* (2013.01)

(56) References Cited

U.S. PATENT DOCUMENTS

| | | | | |
|---|---|---|---|---|
| 10,231,793 | B2* | 3/2019 | Romo | A61B 1/307 |
| 2004/0097806 | A1* | 5/2004 | Hunter | A61B 1/00071 |
| | | | | 600/434 |
| 2006/0252993 | A1* | 11/2006 | Freed | A61B 1/0052 |
| | | | | 604/95.04 |
| 2007/0135803 | A1* | 6/2007 | Belson | A61B 1/00154 |
| | | | | 606/1 |
| 2011/0282151 | A1* | 11/2011 | Trovato | G06T 7/74 |
| | | | | 600/117 |
| 2012/0302875 | A1* | 11/2012 | Kohring | A61B 1/05 |
| | | | | 600/424 |
| 2012/0302878 | A1* | 11/2012 | Liu | A61B 5/064 |
| | | | | 600/424 |
| 2013/0197357 | A1* | 8/2013 | Green | A61B 90/361 |
| | | | | 600/424 |
| 2017/0119412 | A1* | 5/2017 | Noonan | A61B 1/307 |
| 2017/0119474 | A1* | 5/2017 | Kronman | A61B 1/00006 |
| 2018/0296281 | A1* | 10/2018 | Yeung | A61B 34/32 |
| 2019/0142528 | A1* | 5/2019 | Vertikov | A61B 34/20 |
| | | | | 600/424 |
| 2020/0093543 | A1* | 3/2020 | Takahashi | A61B 6/00 |
| 2020/0268364 | A1* | 8/2020 | Watanabe | A61B 1/00016 |
| 2020/0281454 | A1* | 9/2020 | Refai | A61B 90/39 |
| 2021/0052140 | A1* | 2/2021 | Tata | A61B 1/0016 |
| 2021/0059765 | A1* | 3/2021 | Ye | G06V 10/764 |
| 2021/0378759 | A1* | 12/2021 | Komp | A61B 90/36 |

OTHER PUBLICATIONS

W. Jiang, T. Yu, X. He, Y. Yang, Z. Wang and H. Liu, "Data-Driven Modeling the Nonlinear Backlash of Steerable Endoscope Under a Large Deflection Cannulation in ERCP Surgery," 2021 IEEE International Conference on Real-time Computing and Robotics (RCAR), Xining, China, 2021, pp. 39-44, doi: 10.1109/RCAR52367.2021.*
Jaramaz WO2022/076790 A1 Apr. 14, 2022.*

* cited by examiner

SURGICAL SYSTEMS AND DEVICES, AND METHODS FOR CONFIGURING SURGICAL SYSTEMS AND PERFORMING ENDOSCOPIC PROCEDURES, INCLUDING ERCP PROCEDURES

TECHNICAL FIELD

The present disclosure relates generally to surgical systems and devices, and methods for configuring surgical systems and performing surgical actions, and more specifically, to surgical systems, subsystems, processors, devices, logic, methods, and processes for performing biliopancreatic endoscopy and other forms of endoscopy.

BACKGROUND

Endoscopic retrograde cholangiopancreatography (ERCP) remains the gold standard for pathological diagnosis and therapeutic interventions in the biliopancreatic system. During an ERCP procedure, a flexible side-viewing duodenoscope is inserted through a patient's mouth and into the second portion of the patient's duodenum. The endoscopist (also referred to herein as a "surgeon" or "user") then performs cannulation of the major (or minor) papilla (or papillary orifice).

BRIEF SUMMARY

In general, conventional endoscopic procedures are prone to complications. Challenges or difficulties include, but are not limited to, reaching the papilla or the bilioenteric/pancreatoenteric anastomosis; performing cannulation of the biliopancreatic system; and prevention or minimization of post-procedure complications. Surgeons have realized that successful cannulation does not merely imply access to the desired duct, but also requires accomplishing the cannulation in the most efficient and safe manner while minimizing complications.

Present example embodiments relate generally to and/or include systems, subsystems, processors, devices, logic, methods, and processes for addressing conventional problems, including those described above and in the present disclosure, and more specifically, example embodiments relate to systems, subsystems, processors, devices, logic, methods, and processes for performing surgical actions, including biliopancreatic endoscopy and other forms of endoscopy.

In an exemplary embodiment, a method of configuring a surgical system is described. The method includes providing a surgical system. The surgical system includes a main assembly. The main assembly includes a main body for inserting into a cavity of a patient. The main assembly also includes an inertial measurement unit (IMU) subsystem housed in the main body. The main assembly also includes an image capturing subsystem housed in the main body. The main assembly also includes a scope head assembly housed in the main body. The scope head assembly includes a proximal end and a distal end. The scope head assembly is configured to selectively extend the distal end of the scope head assembly outwardly from the main body. At least a portion of the scope head assembly is configured to selectively bend in a plurality of directions. The surgical system also includes a processor. The processor is configured to receive and process communications from the IMU subsystem and the image capturing subsystem. The method also includes capturing, by the image capturing subsystem, real-time images. The method also includes obtaining, by the IMU subsystem, real-time IMU information. The real-time IMU information includes real-time 3-dimensional position information. The method also includes processing, by the processor, the obtained images and IMU information. The processing includes determining whether or not the obtained images include the distal end of the scope head assembly. The processing also includes, responsive to a determination that the obtained images include the distal end of the scope head assembly, identifying the distal end of the scope head assembly in the obtained images and generating, based on the IMU information, real-time 3-dimensional positions of the distal end of the scope head assembly. The processing also includes determining whether or not the obtained images include a cannulation target. When the obtained images are determined, by the processor, to include the cannulation target, the processing also includes identifying the cannulation target in the obtained images and generating, based on the IMU information and the obtained images, real-time 3-dimensional positions of the cannulation target. When the obtained images are determined, by the processor, to include the distal end of the scope head assembly and the cannulation target, the processing also includes predicting, based on the 3-dimensional position of the distal end of the scope head assembly and the 3-dimensional position of the cannulation target, one or more real-time trajectory paths for the identified distal end of the scope head assembly to cannulate the identified cannulation target.

In another exemplary embodiment, a method of configuring a surgical system is described. The method includes providing a surgical system. The surgical system includes a main assembly. The main assembly includes a main body for inserting into a cavity of a patient. The main assembly also includes an inertial measurement unit (IMU) subsystem housed in the main body. The main assembly also includes an image capturing subsystem housed in the main body. The main assembly also includes a scope head assembly housed in the main body. The scope head assembly includes a proximal end and a distal end. The scope head assembly is configured to selectively extend the distal end of the scope head assembly outwardly from the main body. At least a portion of the scope head assembly is configured to selectively bend in a plurality of directions. The surgical system also includes a processor. The processor is configured to receive and process communications from the IMU subsystem and the image capturing subsystem. The method includes generating, by the processor, a plurality of information sets, including a first information set and a second information set. Each of the plurality of information sets include real-time information. The first information set includes a first set of images captured by the image capturing subsystem at a first time instance; and a first set of IMU information obtained, by the processor, from the IMU subsystem at the first time instance. The first set of IMU information includes 3-dimensional position information at the first time instance. The second information set includes a second set of images captured by the image capturing subsystem at a second time instance, the second time instance being a time after the first time instance; and a second set of IMU information obtained, by the processor, from the IMU subsystem at the second time instance. The second set of IMU information includes 3-dimensional position information at the second time instance. The method also includes processing, by the processor, the plurality of information sets, including the first information set and the second information set. The processing includes processing the first information set. The processing of the first information set includes determining whether or not the first set of images include the distal end of the scope head assembly. The processing of the first information set also includes, responsive to a determination that the first set of images include the distal end of the scope head assembly, identifying, for the first time instance, the distal end of the scope head assembly in the first set of images; and generating, based on the first set of IMU information, a 3-dimensional position of the identified distal end of the scope head assembly for the first time instance. The processing of the first information set also includes determining whether or not the first set of images include a cannulation target. When the first set of images is determined, by the processor, to include the cannulation target, the processing of the first information set includes identifying, for the first time instance, the cannulation target in the first set of images; and generating, based on the first set of IMU information and the first set of images, a 3-dimensional position of the identified cannulation target for the first time instance. When the first set of images is determined to include the identified distal end of the scope head assembly and the identified cannulation target, the processing of the first information set includes performing a first prediction. The first prediction is a prediction, based on the 3-dimensional position of the identified distal end of the scope head assembly at the first time instance and the 3-dimensional position of the identified cannulation target at the first time instance, of one or more trajectory paths, for the first time instance, for the identified distal end of the scope head assembly to cannulate the identified cannulation target. The processing also includes processing of the second information set. The processing of the second information set includes determining whether or not the second set of images include the distal end of the scope head assembly. The processing of the second information set includes, responsive to a determination that the second set of images include the distal end of the scope head assembly, identifying, for the second time instance, the distal end of the scope head assembly in the second set of images; and generating, based on the second set of IMU information, a 3-dimensional position of the identified distal end of the scope head assembly for the second time instance. The processing of the second information set includes determining whether or not the second set of images include a cannulation target. When the second set of images is determined, by the processor, to include the cannulation target, the processing of the second information set includes identifying, for the second time instance, the cannulation target in the second set of images; and generating, based on the second set of IMU information and the second set of images, a 3-dimensional position of the identified cannulation target for the second time instance. When the second set of images is determined, by the processor, to include the identified distal end of the scope head assembly and the identified cannulation target, the processing of the second information set includes performing a second prediction. The second prediction is a prediction, based on the 3-dimensional position of the identified distal end of the scope head assembly at the second time instance and the 3-dimensional position of the identified cannulation target at the second time instance, of one or more trajectory paths, for the second time instance, for the identified distal end of the scope head assembly to cannulate the identified cannulation target.

In another exemplary embodiment, a surgical system is described. The surgical system includes a main assembly. The main assembly includes a main body for inserting into a cavity of a patient. The main assembly also includes an inertial measurement unit (IMU) subsystem housed in the main body. The IMU subsystem is configured to provide real-time IMU information, including real-time 3-dimensional position information; The main assembly also includes an image capturing subsystem housed in the main body. The image capturing subsystem is configured to capture real-time images. The main assembly also includes a scope head assembly housed in the main body. The scope head assembly includes a proximal end and a distal end. The scope head assembly is configured to selectively extend the distal end of the scope head assembly outwardly from the main body. At least a portion of the scope head assembly is configured to selectively bend in a plurality of directions. The surgical system also includes a processor. The processor is configured to receive the real-time IMU information from the IMU subsystem. The processor is also configured to receive the real-time images from the image capturing subsystem. The processor is also configured to determine whether or not the received images include the distal end of the scope head assembly. When the received images are determined, by the processor, to include the distal end of the scope head assembly, the processor is configured to identify the distal end of the scope head assembly in the obtained images; and generate, based on the received IMU information, real-time 3-dimensional positions of the distal end of the scope head assembly. The processor is also configured to determine whether or not the received images include a cannulation target. When the received images are determined, by the processor, to include the cannulation target, the processor is configured to identify the cannulation target in the received images; and generate, based on the IMU information and the received images, real-time 3-dimensional positions of the cannulation target. When the received images are determined, by the processor, to include the distal end of the scope head assembly and the cannulation target, the processor is configured to predict, based on the 3-dimensional position of the distal end of the scope head assembly and the 3-dimensional position of the cannulation target, one or more real-time trajectory paths for the identified distal end of the scope head assembly to cannulate the identified cannulation target.

BRIEF DESCRIPTION OF THE FIGURES

For a more complete understanding of the present disclosure, example embodiments, and their advantages, reference is now made to the following description taken in conjunction with the accompanying figures, in which like reference numbers indicate like features, and.

Although similar reference numbers may be used to refer to similar elements in the figures for convenience, it can be appreciated that each of the various example embodiments may be considered to be distinct variations.

Figure 1A:
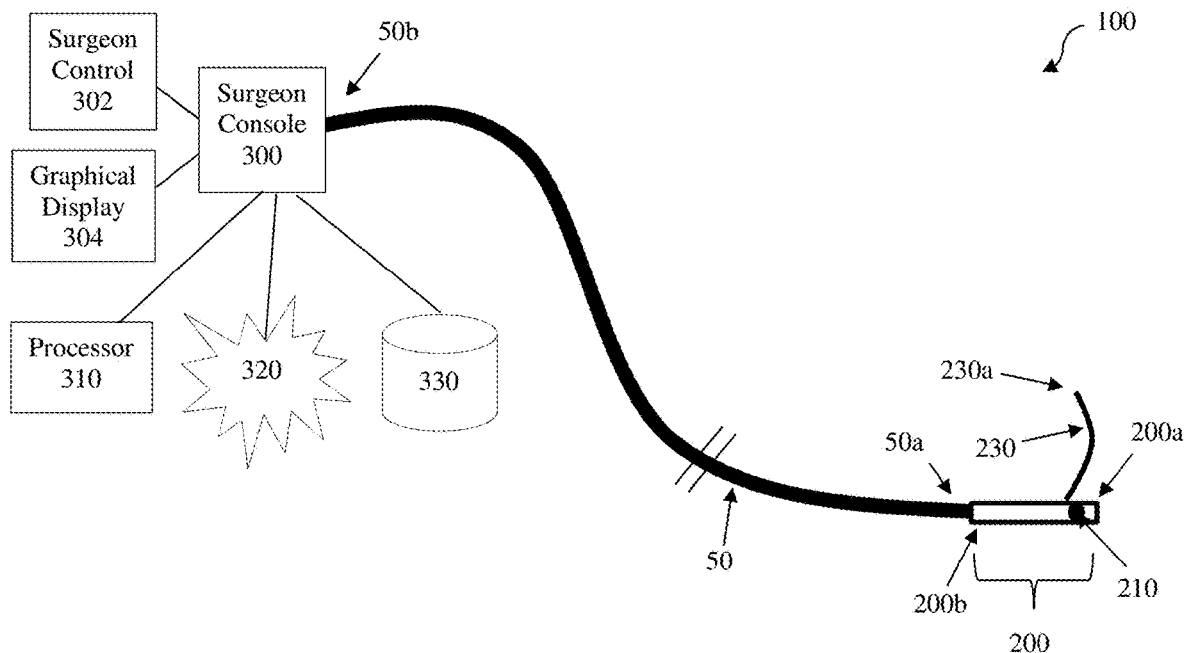
FIG. 1A is an illustration of an example embodiment of a surgical system.

Example embodiments will now be described with reference to the accompanying figures, which form a part of the present disclosure and which illustrate example embodiments which may be practiced. As used in the present disclosure and the appended claims, the terms "embodiment", "example embodiment", "exemplary embodiment", and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on", and the terms "a", "an", and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon", depending on the context. Furthermore, as used in the present disclosure and the appended claims, the words "and/or" may refer to and encompass any and all possible combinations of one or more of the associated listed items. Furthermore, as used in the present disclosure and the appended claims, the words "real time", "real-time", or the like, may refer to receiving in real time or near real time, accessing in real time or near real time, transmitting in real time or near real time, making available in real time or near real time, processing in real time or near real time, and/or storing in real time or near real time (each as applicable).

DETAILED DESCRIPTION

Conventional endoscopic procedures, including ERCP procedures, are generally prone to complications, even in the hands of experienced surgeons. For example, challenges in performing ERCP procedures include, but are not limited to, difficulties in appropriately positioning and orientating the duodenoscope in front of the papilla or the bilioenteric/pancreatoenteric anastomosis; difficulties in performing cannulation of the biliopancreatic system; and difficulties in preventing complications (post-procedure). Surgeons have realized that successful cannulation does not merely imply access to the desired duct, but also requires accomplishing the cannulation in the most efficient and safe manner while minimizing post-procedure complications, especially post-ERCP pancreatitis (or PEP). A major drawback of conventional ERCP techniques is that it relies on indirect visualization of the bile duct. Furthermore, the diagnosis of biliary lesions (e.g., stones, strictures) and their anatomical location(s) rely on inexactly targeted sampling and/or 2-dimensional imaging, which provide poor sensitivity rates when it comes to diagnosing malignancy.

Present example embodiments relate generally to and/or include systems, subsystems, processors, devices, logic, methods, and processes for addressing conventional problems, including those described above and in the present disclosure. As will be further described in the present disclosure, present example embodiments relate to surgical systems, subsystems, processors, devices, logic, methods, and processes for performing surgical actions including, but not limited to, one or more of the following: capturing and processing of real-time images (which includes video images and/or still images) captured by an image capturing subsystem 210; measuring and processing of real-time measurements (also referred to herein as "IMU information") measured from an IMU subsystem 220 (i.e., processing in real-time); processing, in real-time, of images to determine whether or not the images include the capturing of an image of a scope head assembly 230 (e.g., determine whether the scope head assembly 310 is within the image capturing view of the image capturing subsystem 210); processing, in real-time, of the images to determine whether or not the images include a distal end 230a of the scope head assembly 230; identifying, in real-time, the distal end 230a of the scope head assembly 230 in the images; generating (and/or drawing, adding, superimposing, and/or overlaying), in images that are to be displayed on a graphical display 304, of a visible indicator, or the like, for the distal end 230a of the scope head assembly 230; generating of real-time 3-dimensional positions (e.g., Cartesian coordinates) of the distal end 230a of the scope head assembly 230 when the images are determined to include the distal end 230a of the scope head assembly 230 (i.e., generating in real-time); generating of real-time depth information for the distal end 230a of the scope head assembly 230 (e.g., depth or distance information between the distal end 230a of the scope head assembly 230 and a reference point on the main assembly 200) (i.e., generating in real-time); processing, in real-time, of the images to determine whether or not the images include a cannulation target (e.g., when performing an ERCP procedure, the cannulation target may be a papilla or papillary orifice that opens up into the common bile duct (CBD) and the pancreatic bile duct; it is to be understood that other procedures and other cannulation targets are also contemplated without departing from the teachings of the present disclosure); identifying, in real-time, of the cannulation target in the images; generating (and/or drawing, adding, superimposing, and/or overlaying), in the images that are to be displayed on the graphical display 304, a visible indicator, or the like, for the cannulation target (i.e., generating in real-time); generating of real-time 3-dimensional positions (e.g., Cartesian coordinates) of the cannulation target when the images are determined to include the cannulation target (i.e., generating, in real-time); generating of real-time depth information for the cannulation target (e.g., depth or distance information between the cannulation target and a reference point on the main assembly 200) (i.e., generating in real-time); generating of a predicted real-time trajectory path 20 for the distal end 230a of the scope head assembly 230 when the images are determined to include at least the distal end 230a of the scope head assembly 230 (i.e., generating in real-time); generating of a predicted real-time post-cannulation trajectory path 10 for the cannulation target when the images are determined to include at least the cannulation target (i.e., generating in real-time); generating of a predicted real-time trajectory path 20 and/or predicted real-time post-cannulation trajectory path 10 for the distal end 230a of the scope head assembly 230 to cannulate the cannulation target when the images are determined to include both the distal end 230a of the scope head assembly 230 and the cannulation target (i.e., generating in real-time); displaying, on a graphical display, a predicted real-time trajectory path 20 for the distal end 230a of the scope head assembly 230 when the images are determined to include at least the distal end 230a of the scope head assembly 230 (i.e., displaying in real-time); displaying, on a graphical display, a predicted real-time post-cannulation trajectory path 10 for the cannulation target when the images are determined to include at least the cannulation target (i.e., displaying in real-time); displaying, on a graphical display, a predicted real-time trajectory path 20 and/or predicted real-time post-cannulation trajectory path 10 for the distal end 230a of the scope head assembly 230 to cannulate the cannulation target when the images are determined to include both the distal end 230a of the scope head assembly 230 and the cannulation target (i.e., displaying in real-time); and/or generating of real-time depth information between the cannulation target and the distal end 230a of the scope head assembly 230.

Although example embodiments described in the present disclosure may be mostly directed to biliopancreatic endoscopy, it is to be understood that example embodiments may also be directed and/or applied to other forms of endoscopy including, but not limited to, bronchoscopy, colonoscopy, colposcopy, cystoscopy, esophagealgastroduodenoscopy (EGD), laparoscopy, laryngoscopy, proctoscopy, thoracoscopy, brochoscopy.

Example embodiments will now be described below with reference to the accompanying figures, which form a part of the present disclosure.

Example Embodiments of a Surgical System for Performing Endoscopy (e.g., Surgical System 100).

Figure 1B:
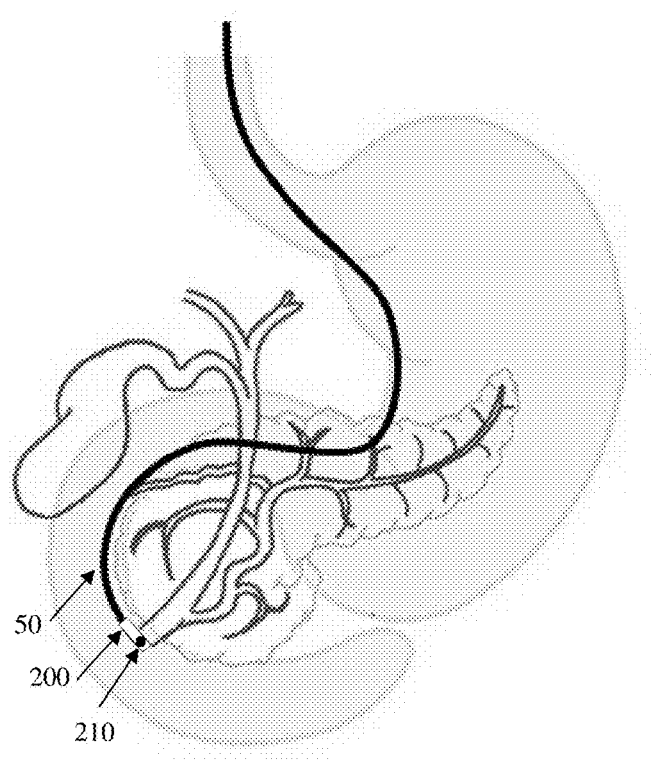
FIG. 1B is an illustration of an example embodiment of a surgical system provided through a patient's mouth and into the patient's duodenum.

FIG. 1A illustrates an example embodiment of a surgical system (e.g., surgical system 100) for performing a surgical procedure, such as an endoscopic procedure. For example, as illustrated in FIG. 1B, the surgical system 100 may be configurable or configured to perform endoscopic retrograde cholangiography and pancreatography (ERCP). It is to be understood in the present disclosure that example embodiments of the surgical system 100 may also be configurable or configured to perform other surgical actions including, but not limited to, bronchoscopy, colonoscopy, colposcopy, cystoscopy, endoscopic esophagealgastroduodenoscopy (EGD), laparoscopy, laryngoscopy, proctoscopy, thoracoscopy, brocho scopy etc.

To perform the actions, functions, processes, and/or methods described above and in the present disclosure, example embodiments of the surgical system 100 include one or more elements. For example, the surgical system 100 includes a main assembly (e.g., main assembly 200) provided at a distal end of the surgical system 100 (e.g., distal relative to the surgeon console 300). The main assembly 200 includes a proximal end 200b and a distal end 200a. The main assembly 200 is configurable or configured to be inserted into a cavity of a patient (e.g., through a patient's mouth and into the second portion of the patient's duodenum).

The surgical system 100 also includes an elongated tubular member (e.g., elongated tubular member 50), or the like, having a proximal end 50b and a distal end 50a. The distal end 50a of the elongated tubular member 50 is configurable or configured to bend in one or more of a plurality of directions. Such bending of the distal end 50a of the elongated tubular member 50 is controllable by the surgeon via a surgeon console or controller (e.g., surgeon console 300). The distal end 50a of the elongated tubular member 50 is securable or secured to a proximal end 200b of the main assembly 200.

The surgical system 100 also includes a surgeon console (e.g., surgeon console 300) connected to the proximal end 50b of the elongated tubular member 50. The surgeon console 300 may include, be a part of, and/or be in communication with one or more processors (e.g., processor 310), one or more surgeon controls (e.g., surgeon control 302), one or more graphical displays (e.g., graphical display 304), one or more communication channels or networks (e.g., communication channel 320 or network 320), and/or one or more databases (e.g., database 330).

As used in the present disclosure, when applicable, a reference to a surgical system 100 (and/or one or more of its elements), surgeon console 300 (and/or one or more of its elements), and/or processor 310 (and/or one or more of its elements) may also refer to, apply to, and/or include one or more computing devices, processors, servers, systems, cloud-based computing, or the like, and/or functionality of one or more processors, computing devices, servers, systems, cloud-based computing, or the like. The surgical system 100 (and/or one or more of its elements), surgeon console 300 (and/or one or more of its elements), and/or processor 310 (and/or one or more of its elements) may be or have any processor, server, system, device, computing device, controller, microprocessor, microcontroller, microchip, semiconductor device, or the like, configurable or configured to perform, among other things, 3-dimensional positioning determination and control of one or more elements of the surgical system 100; 3-dimensional orientation determination and control of one or more elements of the surgical system 100; speed, velocity, vector, and/or acceleration determination and control of one or more elements of the surgical system 100; movement direction determination and control of one or more elements of the surgical system 100; image capturing (including video image and still image capturing); image processing (including automated image processing of video images and still images); feature extraction (including extraction of features from video images and still images); 3-dimensional position determination of a papilla, opening, or other part of a patient; depth estimation, determination, and control (including 3-dimensional depth estimation, determination, and control); trajectory path prediction, generation, and control (including 3-dimensional trajectory path prediction, generation, and control); and/or any one or more other actions, functions, methods, and/or processes described above and in the present disclosure. Alternatively, or in addition, the surgical system 100 (and/or one or more of its elements), surgeon console 300 (and/or one or more of its elements), and/or processor 310 (and/or one or more of its elements) may include and/or be a part of a virtual machine, processor, computer, node, instance, host, or machine, including those in a networked computing environment.

As used in the present disclosure, a communication channel 320, network 320, cloud 320, or the like, may be or include a collection of devices and/or virtual machines connected by communication channels that facilitate communications between devices and allow for devices to share resources. Such resources may encompass any types of resources for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof. A communication channel 320, network 320, cloud 320, or the like, may include, but is not limited to, computing grid systems, peer to peer systems, mesh-type systems, distributed computing environments, cloud computing environment, video/image communication channels, etc. Such communication channels 320, networks 320, clouds 320, or the like, may include hardware and/or software infrastructures configured to form a virtual organization comprised of multiple resources which may or may not be in geographically disperse locations. Communication channel 320, network 320, cloud 320, or the like, may also refer to a communication medium between processes on the same device. Also as referred to herein, a processor 310, network element, node, or server may be a device deployed to execute a program operating as a socket listener and may include software instances.

These and other elements of the surgical system 100 will now be further described with reference to the accompanying figures.

The Elongated Tubular Member (e.g., Elongated Tubular Member 50).

As illustrated in at least FIG. 1A, the surgical system 100 includes an elongated tubular member (e.g., elongated tubular member 50). The elongated tubular member 50 includes a proximal end 50b and a distal end 50a. The elongated tubular member 50 is configurable or configured to cooperate with, communicate with, and/or be controlled and/or managed by a surgeon and/or one or more elements of the surgical system 100, including the surgeon console 300, surgeon control 302, graphical display 304, processor 310, network 320, and/or database 330, so as to perform a variety of actions and/or functions described in the present disclosure. For example, the elongated tubular member 50 is configurable or configured to advance the main assembly 200 through a cavity of a patient (e.g., through the patient's mouth and into the second portion of the patient's duodenum). The elongated tubular member 50 is also configurable or configured to advance the main assembly 200 (which is secured to the distal end 50a of the elongated tubular member 50) around flexural, looping, and/or bending sections of the cavities of the patient by selectively controlling a bending location, bending angle, bending direction, and/or bending location of at least a portion of a distal end 50a of the elongated tubular member 50.

To perform the actions, functions, processes, and/or methods described above and in the present disclosure, example embodiments of the elongated tubular member 50 include one or more elements. For example, the elongated tubular member 50 includes one or more interior channels. Such interior channels may be configured for the passing and/or housing of communication/data cables, including cables for the communication of video images and/or still images from the image capturing subsystem 210 to the processor 310 and/or one or more other elements of the surgical system 100; and/or cables for the communication of IMU measurements from the IMU subsystem 220 to the processor 310 and/or one or more other elements of the surgical system 100. Alternatively or in addition, such interior channels may be configured for the passing and/or housing of power cables (e.g., for providing power to the image capturing subsystem 210, illumination source(s) (not shown), and/or the IMU subsystem 220). Alternatively or in addition, such interior channels may be configured for the passing and/or housing of a proximal end (not shown) of the scope head assembly 230 and/or other control members (not shown) configurable or configured to control movements and/or orientation of the scope head assembly 230 (e.g., forward movement or extension; backward movement or contraction; bending location, bending angle, and/or bending direction of at least a portion of the distal end 230a of the scope head assembly 230; etc.). Alternatively or in addition, such interior channels may be configured for the passing and/or housing of cables, wires, or the like, for controlling the bending location, bending angle, and/or bending direction of at least a portion of the distal end 50a of the elongated tubular member 50. The distal end 50a of the elongated tubular member 50 may include a plurality of bending members 50c or sections 50c, which receive and/or are secured to one or more such cables, wires, or the like, that control the bending location, bending angle, and/or bending direction of at least one portion of the distal end 50a of the elongated tubular member 50. In some example embodiments, the distal end 50a of the elongated tubular member 50 may also include one or more expandable members (or balloons) (not shown) and/or one or more negative pressure openings (not shown), which may be used for anchoring of the distal end 50a of the elongated tubular member 50 to an interior wall of a cavity of a patient (e.g., when the main assembly 200 has reached an ideal, target, and/or preferred 3-dimensional position and orientation, such as in front of a papilla, and the surgical system 100 is ready to extend the scope head assembly 230 to perform a cannulation of the papilla).

Although the actions, functions, processes, and/or methods performed by the elongated tubular member 50 may be described in the present disclosure as being performed by one or more particular elements of the elongated tubular member 50, the actions, functions, processes, and/or methods performed by a particular element of the elongated tubular member 50 may also be performed by one or more other elements and/or cooperatively performed by more than one element of the elongated tubular member 50 (and/or other elements of the surgical system 100) without departing from the teachings of the present disclosure. It is also to be understood in the present disclosure that, although the actions, functions, processes, and/or methods performed by the elongated tubular member 50 are described in the present disclosure as being performed by particular elements of the elongated tubular member 50, the actions, functions, processes, and/or methods performed by two or more particular elements of the elongated tubular member 50 may be combined and performed by one element of the elongated tubular member 50 without departing from the teachings of the present disclosure.

The Main Assembly (e.g., Main Assembly 200).

As illustrated in at least FIGS. 1-4, the surgical system 100, which is configurable or configured to perform surgical actions, including, but not limited to, an endoscopic retrograde cholangiopancreatography (ERCP) cannulation, includes one or more main assemblies (e.g., main assembly 200). The main assembly 200 includes a proximal end 200b and a distal end 200a. The proximal end 200b of the main assembly 200 is secured to the distal end 50a of the elongated tubular member 50. The main assembly 200 is configurable or configured to cooperate with, communicate with, and/or be controlled and/or managed by one or more elements of the surgical system 100, including the surgeon console 300, surgeon control 302, graphical display 304, processor 310, network 320, and/or database 330, to perform a variety of actions and/or functions.

For example, the main assembly 200 is configurable or configured to perform 3-dimensional positioning determination and control of one or more elements of the surgical system 100 (e.g., determination and control of 3-dimensional positioning (e.g., in Cartesian coordinates, etc.) of the scope head assembly 230 and/or the distal end 50a of the elongated tubular member 50). As another example, the main assembly 200 is configurable or configured to perform 3-dimensional orientation determination and control of one or more elements of the surgical system 100 (e.g., determination and control of 3-dimensional orientation of the scope head assembly 230 and the distal end 50a of the elongated tubular member 50). As another example, the main assembly 200 is configurable or configured to perform speed, velocity, and/or acceleration determination and control of one or more elements of the surgical system 100 (e.g., determination and control of speed, velocity, and/or acceleration of the scope head assembly 230 and the distal end 50a of the elongated tubular member 50). As another example, the main assembly 200 is configurable or configured to perform movement direction determination and control of one or more elements of the surgical system 100 (e.g., determination and control of movement direction of the scope head assembly 230 and the distal end 50a of the elongated tubular member 50). As another example, the main assembly 200 is configurable or configured to perform image capturing (including capturing of video images and still images via an image capturing subsystem 210). As another example, the main assembly 200 is configurable or configured to perform image processing (including automated image processing of video images and still images via the processor 310 and/or network 320). As another example, the main assembly 200 is configurable or configured to perform feature identification, extraction, classification, and/or size estimation (including identification, extraction, classification, and/or size estimation of features, such as a papilla, cavity opening, cavity wall, lesion, distal end 230a of the scope head assembly 230, etc., based on, among other things, historic and/or real time video images, still images, and/or IMU subsystem 220 measurements via the processor 310 and/or network 320). As another example, the main assembly 200 is configurable or configured to perform 3-dimensional position estimation and/or determination (e.g., in Cartesian coordinates, etc.) of a feature (including 3-dimensional position estimation and/or determination of features, such as a papilla, cavity opening, cavity wall, lesion, and/or other part of a patient, based on, among other things, historic and/or real time video images, still images, and/or IMU subsystem 220 measurements via the processor 310 and/or network 320). As another example, the main assembly 200 is configurable or configured to perform 3-dimensional depth estimation, determination, and control (including 3-dimensional depth estimation, determination, and control of a feature, such as a papilla, cavity opening, cavity wall, lesion, distal end 230a of the scope head assembly 230, etc., based on, among other things, historic and/or real time video images, still images, and/or IMU subsystem 220 measurements via the processor 310 and/or network 320). As another example, the main assembly 200 is configurable or configured to perform trajectory path prediction, determination, generation, and control (including 3-dimensional trajectory path prediction, generation, and control of the scope head assembly 230 based on, among other things, historic and/or real time video images, still images, and/or IMU subsystem 220 measurements via the processor 310 and/or network 320); and/or any one or more other actions, functions, methods, and/or processes described above and in the present disclosure.

Figure 4A:
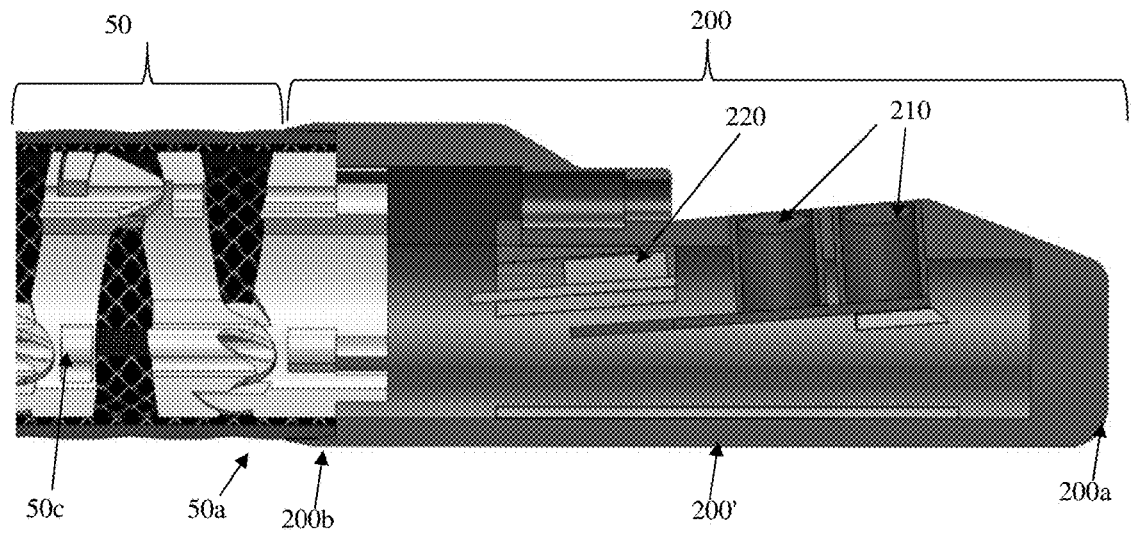
FIG. 4A is an illustration of a cross-sectional view of an example embodiment of a main assembly having two image capturing assemblies.
Figure 4B:
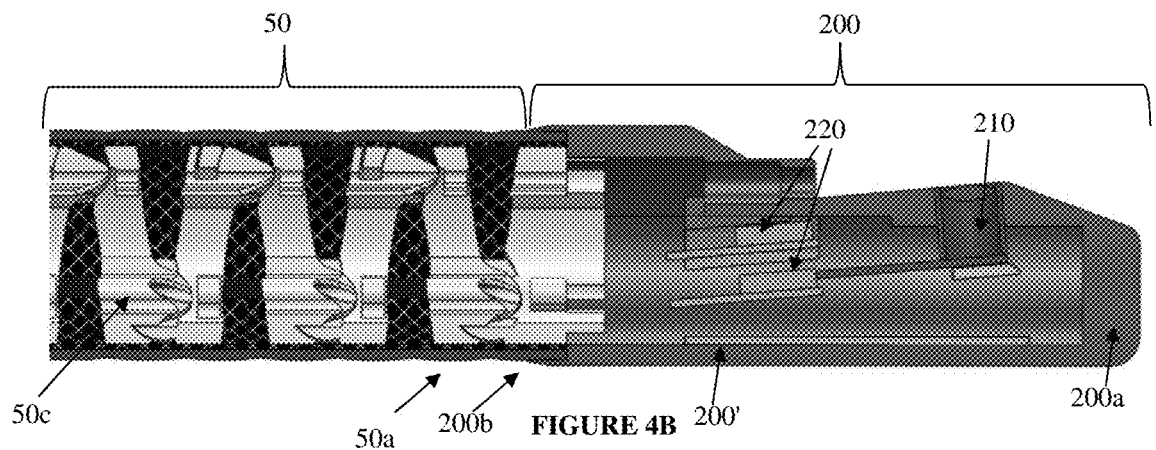
FIG. 4B is an illustration of a cross-sectional view of an example embodiment of a main assembly having two IMU assemblies and an image capturing assembly.

To perform the actions, functions, processes, and/or methods described above and in the present disclosure, example embodiments of the main assembly 200 include one or more elements. For example, as illustrated in the perspective views of FIG. 2A, FIG. 2B, FIG. 2C, and FIG. 2D and the cross-sectional side views of FIG. 3A and FIG. 3B, the main assembly 200 includes a main body 200', as well as a proximal end 200b and a distal end 200a. The main assembly 200 also includes one or more image capturing subsystems 210. For example, as illustrated in at least FIGS. 2A-D and 3A-B, the main assembly 200 may include a single image capturing subsystem 210 (e.g., a monocular duodenoscope, or the like) housed in the main body 200'. As another example, as illustrated in FIG. 4A, the main assembly 200 may include two (or more) image capturing subsystems 210 housed in the main body 200'. The main assembly 200 also includes one or more inertial measurement unit (IMU) subsystems 220. For example, as illustrated in at least FIGS. 2C-D and 3A-B, the main assembly 200 may include a single IMU subsystem 220 housed in the main body 200'. As another example, as illustrated in FIG. 4B, the main assembly 200 may include two (or more) inertial measurement unit (IMU) subsystems 210 housed in the main body 200'. The main assembly 200 also includes one or more scope head assemblies 230. For example, as illustrated in at least FIGS. 2A-D and 3A-B, the main assembly 200 may include a single scope head assembly 230 that is extendible outwardly from the main body 200' (as illustrated in at least FIGS. 2B, 2D, and 3C).

Although the actions, functions, processes, and/or methods performed by the main assembly 200 may be described in the present disclosure as being performed by one or more particular elements of the main assembly 200, the actions, functions, processes, and/or methods performed by a particular element of the main assembly 200 may also be performed by one or more other elements and/or cooperatively performed by more than one element of the main assembly 200 (and/or other elements of the surgical system 100) without departing from the teachings of the present disclosure. It is also to be understood in the present disclosure that, although the actions, functions, processes, and/or methods performed by the main assembly 200 are described in the present disclosure as being performed by particular elements of the main assembly 200, the actions, functions, processes, and/or methods performed by two or more particular elements of the main assembly 200 may be combined and performed by one element of the main assembly 200 without departing from the teachings of the present disclosure.

These elements of the main assembly 200 will now be further described with reference to the accompanying figures.

The Image Capturing Subsystem (e.g., Image Capturing Assembly 210 or Image Capturing Subsystem 210).

In an example embodiment, the main assembly 200 includes one or more image capturing subsystems (e.g., image capturing assembly 210 or image capturing subsystem 210). As illustrated in at least FIGS. 1-4, the image capturing subsystem 210 is housed in the main body 200' of the main assembly 200, and the main body 200' includes an opening for each camera 210 of the image capturing subsystem 210. The image capturing subsystem 210 may be any image capturing device or system configurable or configured to capture video and/or still images. For example, the image capturing subsystem 210 may include a single camera 210 (e.g., as in a monocular duodenoscope, or the like) for capturing a single view of video and/or still images.

The image capturing subsystem 210 is configurable or configured to be in wired and/or wireless communications with the surgeon console 300, surgeon control 302, graphical display 304, processor 310, network 320, database 330, and/or one or more other elements of the surgical system 100. For example, in operation, the image capturing subsystem 210 is configured to transmit real-time video images and/or still images (also referred to in the present disclosure simply as "images") to the processor 310, which processes the images (which may including processing along with data received from the IMU subsystem 220, actions performed by the surgeon via the surgeon control 302 and/or console 300 as detected by the processor 310, and/or historic information from one or more databases 330) in real-time and displays the images on the graphical display 304 for the surgeon to view. As will be further described in the present disclosure, processing by the processor 310 may be performed alone or in cooperation with one or more networks 320, databases 330, and/or other processors (not shown), such as in example embodiments wherein one or more actions or functions of the surgical system 100 (e.g., including, but not limited to, one or more of the following: image pre-processing, processing and displaying; feature identification, extraction, classification, and/or size estimation; 3-dimensional position determination; 3-dimensional orientation determination; speed, velocity, and/or acceleration determination; movement direction determination; 3-dimensional depth estimation; trajectory path prediction, determination, and control) are performed by one or more elements of the surgical system 100 based on such processing by the processor 310 and/or calculations, estimations, results, inferences, predictions, or the like, generated and/or derived, directly or indirectly, partially, in cooperation or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SIAM), etc. Furthermore, such artificial intelligence (AI) algorithms, engines, systems, processors, and/or processes may be provided locally via the processor 310 (and/or one or more elements of the processor 310 and/or surgical system 100) and/or via cloud computing 310, distributed computing 310, and/or non-localized or decentralized artificial intelligence (AI) 310, etc.

Although example embodiments of the image capturing subsystem 210 are mostly described in the present disclosure as having one camera 210 (see, for example, FIGS. 1-3), it is to be understood that example embodiments of the image capturing subsystem 210 may include two (or more) cameras 210 (see, for example, FIG. 4A). Such example embodiments having two or more cameras 210 are recognized in the present disclosure as improving the ability to generate 3-dimensional views on the graphical display 304 and generating depth estimations since two (or more cameras 210) can capture two (or more) slightly different views of video and/or still images. It is recognized in the present disclosure, however, that example embodiments of the image capturing subsystem 210 having a single camera 210 for the main assembly 200 also provides advantages including, but not limited to, a reduction in overall hardware size, weight, cost, and one or more dimensions of the main assembly 200 as compared to example embodiments of the image capturing subsystem 210 having two (or more) cameras 210.

The Inertial Measurement Unit (IMU) Subsystem (e.g., IMU Assembly 220 or IMU Subsystem 220).

In an example embodiment, the main assembly 200 includes one or more inertial measurement unit (IMU) assemblies (e.g., IMU assembly 220 or IMU subsystem 220). As illustrated in at least FIGS. 3A-B, the IMU subsystem 220 is housed in the main body 200' of the main assembly 200. The IMU subsystem 220 may be any inertial measurement device or system configurable or configured to perform measurements and/or readings of, among other things, specific force, angular rate, position, and/or orientation using one or more accelerometers, gyroscopes, and/or magnetometers, EM tracker (not shown) of the IMU subsystem 220. For example, the IMU subsystem 220 may include a single IMU device 220 having one or more accelerometers, gyroscopes, magnetometers, and/or EM tracker (not shown).

The IMU subsystem 220 is configurable or configured to be in wired and/or wireless communications with the surgeon console 300, surgeon control 302, graphical display 304, processor 310, network 320, database 330, and/or one or more other elements of the surgical system 100. For example, in operation, the IMU subsystem 220 is configured to transmit real-time measurements and/or readings to the processor 310, which processes the measurements and/or readings (which may include processing along with images received from the image capturing subsystem 210, actions performed by the surgeon via the surgeon control 302 and/or console 300 as detected by the processor 310, and/or historic information from one or more databases 330) in real-time. The IMU subsystem 220 may also provide such IMU measurements to the graphical display 304 to display for the surgeon to view. As will be further described in the present disclosure, processing by the processor 310 may be performed alone or in cooperation with one or more networks 320, databases 330, and/or other processors (not shown), such as in example embodiments wherein one or more actions or functions of the surgical system 100 (e.g., including, but not limited to, one or more of the following: image pre-processing, processing, and displaying; feature identification, extraction, classification, and/or size estimation;

3-dimensional position determination; 3-dimensional orientation determination; speed, velocity, and/or acceleration determination; movement direction determination; 3-dimensional depth estimation; trajectory path prediction, determination, and control) are performed by one or more elements of the surgical system 100 based on such processing by the processor 310 and/or calculations, estimations, results, inferences, predictions, or the like, generated and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the processor 310 (and/or one or more elements of the processor 310 and/or surgical system 100) and/or via cloud computing 310, distributed computing 310, and/or non-localized or decentralized artificial intelligence (AI) 310, etc.

Although example embodiments of the IMU subsystem 220 are mostly described in the present disclosure as having one IMU device 220 (see, for example, FIGS. 3A-B), it is to be understood that example embodiments of the IMU subsystem 220 may include two (or more) IMU devices 220 (see, for example, FIG. 4B). Such example embodiments having two or more IMU devices 220 are recognized in the present disclosure as improving the reliability to generate accurate and reliable measurements and readings, including the ability to provide backup measurements and readings in a situation where one IMU device 220 is not properly functioning (or not functioning at all). It is recognized in the present disclosure, however, that example embodiments of the IMU subsystem 220 having a single IMU device 220 for the main assembly 200 also provides advantages including, but not limited to, a reduction in overall size, weight, and one or more dimensions of the main assembly 200 as compared to example embodiments of the IMU subsystem 220 having two (or more) IMU devices 220.

The Surgeon Console (e.g., Surgeon Console 300).

As illustrated in at least FIG. 1A, the surgical system 100, which is configurable or configured to perform surgical actions, including, but not limited to, an endoscopic retrograde cholangiopancreatography (ERCP) cannulation, includes one or more surgeon consoles (e.g., surgeon console 300). The surgeon console 300 is configurable or configured to provide, among other things, an interface for one or more surgeons to, among other things, view, control, and manage the surgical system 100. The surgeon console 300 is configurable or configured to cooperate with, communicate with, secure to, and/or control and/or manage one or more elements of the surgical system 100, including the elongated tubular member 50 and the main assembly 200. The surgeon console 300 may include and/or be in communication with one or more other elements of the surgical system 100, including one or more surgeon controls 302, one or more graphical displays 304, and/or one or more processors 310. The surgeon console 300 may also include and/or be in communication with one or more networks 320 and/or one or more databases 330.

Although the figures may illustrate one surgeon control 302, one graphical display 304, one processor 310, one network 320, and one database 330, it is to be understood that the surgical system 100 may include more or less than one surgeon control 302, more or less than one graphical display 304, more or less than one processor 310, more or less than one network 320, and more or less than one database 330 without departing from the teachings of the present disclosure.

These elements of and/or in communication with the surgeon console 300 will now be further described with reference to the accompanying figures.

The Surgeon Control (e.g., Surgeon Control 302).

As illustrated in FIG. 1, an example embodiment of the surgeon console 300 includes and/or is in communication with one or more surgeon controls (e.g., surgeon control 302). The surgeon control 302 is configurable or configured to enable the surgeon to control one or more elements, aspects, and/or actions of the elongated tubular member 50 and/or main assembly 200.

For example, the surgeon control 302 may include a joystick, bendable member, touchscreen, buttons, scroll wheel, track ball, turning knob, lever and/or any other actuatable controller for the surgeon to selectively control bending location, bending angle, and/or bending direction of at least a portion of the distal end 50a of the elongated tubular member 50. As another example, the surgeon control 302 may include a joystick, bendable member, touchscreen, buttons, scroll wheel, track ball, turning knob, lever, and/or any other actuatable controller for the surgeon to selectively control a length (e.g., extension outwardly away from the main body 200' of the main assembly 200, contraction inwardly toward the main body 200' of the main assembly 200, fully retracted and housed inside the main body 200' of the main assembly 200, etc.), bending location, bending angle, and/or bending direction of the scope head assembly 230. The surgeon control 302 may also include a joystick, touchscreen, buttons, scroll wheel, track ball, turning knob, lever, and/or any other controller for the surgeon to selectively control operation of the image capturing assembly 210 (and/or each camera 210 of the image capturing assembly 210 in example embodiments having two or more cameras 210), including the capturing and not capturing of images and other functionality/features such as controlling of the focus, zoom, lighting, exposure, etc. of the camera 210 of the image capturing assembly 210. The surgeon control 302 may also include a button, toggle switch, touchscreen, and/or any other controller for the surgeon to selectively control operation of an illumination source (not shown), including the brightness, color, direction, etc. of the illumination source. The surgeon control 302 may also include a button, toggle switch, touchscreen, and/or any other controller for the surgeon to selectively control operation of the IMU subsystem 220 (and/or each IMU device 220 of the IMU subsystem 220 in example embodiments having two or more IMU devices 220).

In example embodiments, surgeon actions performed on the surgeon control 302 may be captured and communicated by and/or to (as applicable) the processor 310, network 320, database 330, and/or one or more other elements of the surgical system 100. For example, the processor 310 (and/or network 320 and/or database 330) may use such information in performing processing, such as image processing and displaying; feature identification, extraction, classification, and/or size estimation; 3-dimensional position determination; 3-dimensional orientation determination; speed, velocity, and/or acceleration determination; movement direction determination; 3-dimensional depth estimation; trajectory path prediction, determination, and control. As another example, the processor 310 (and/or network 320) may store such information in the database 330 for use in future processing (e.g., use as historic information in future processing).

The Graphical Display (e.g., Graphical Display 304).

As illustrated in FIG. 1A, an example embodiment of the surgeon console 300 includes and/or is in communication with one or more graphical displays (e.g., graphical display 304). The graphical display 304 is configurable or configured to display real-time images captured by the image capturing subsystem 210, which may be provided directly from the image capturing subsystem 210 and/or by the processor 310. The graphical display 304 may also be configurable or configured to display real-time 3-dimensional constructed or reconstructed images, data, and/or depth information of the view/images captured by the image capturing subsystem 210 based on the processing, by the processor 310, of images captured by the image capturing subsystem 210 and measurements/readings by the IMU subsystem 220 (and may also include historic information, including historic captured images and/or historic measurements/readings).

The real-time images displayed on the graphical display 304 may also include real-time visual indicators (e.g., bounding box, etc.) of one or more features (e.g., a papilla, cavity opening, cavity wall, lesion, distal end 230a of the scope head assembly 230, etc.) identified, extracted, classified, and/or size-estimated based on feature extraction processing. The real-time images displayed on the graphical display 304 may also include an indication of real-time 3-dimensional positions of one or more elements of the surgical system 100. The real-time images displayed on the graphical display 304 may also include an indication of real-time 3-dimensional orientation of one or more elements of the surgical system 100 (e.g., orientation of the main assembly 200, including orientation of the scope head assembly 230). The real-time images displayed on the graphical display 304 may also include an indication of speed, velocity, and/or acceleration of one or more elements of the surgical system 100 (e.g., speed, velocity, and/or acceleration of the main assembly 200, including speed, velocity, and/or acceleration of the scope head assembly 230). The real-time images displayed on the graphical display 304 may also include an indication of movement direction of one or more elements of the surgical system 100 (e.g., movement direction of the main assembly 200, including movement direction of the scope head assembly 230). The real-time images displayed on the graphical display 304 may also include an indication of real-time 3-dimensional positions of one or more features (e.g., a papilla, cavity opening, cavity wall, lesion, distal end 230a of the scope head assembly 230, etc.) identified, extracted, classified, and/or size-estimated based on feature extraction processing. The real-time images displayed on the graphical display 304 may also include an indication of 3-dimensional depth estimation of one or more features (e.g., a papilla, cavity opening, cavity wall, lesion, distal end 230a of the scope head assembly 230, etc.) identified, extracted, classified, and/or size-estimated based on feature extraction processing. As will be further described in the present disclosure, the real-time images displayed on the graphical display 304 may include real-time 3-dimensional predicted, inferred, and/or estimated trajectory path(s) 20 for a distal end 230a of the scope head assembly 230 based on a current position and/or orientation of the distal end 230a of the scope head assembly 230. The real-time images displayed on the graphical display 304 may also include real-time 3-dimensional predicted, inferred, and/or estimated post-cannulation trajectory path(s) 10 for a cannulation target. The real-time images displayed on the graphical display 304 may also include real-time 3-dimensional predicted, inferred, and/or estimated trajectory path(s) 20 and post-cannulation trajectory path(s) 10 for a distal end 230a of the scope head assembly 230 to successfully reach an identified target or feature (e.g., to successfully perform cannulation of a papilla when performing ERCP cannulation).

The Processor (e.g., Processor 310).

As illustrated in at least FIG. 1A, the surgical system 100 includes one or more processors (e.g., processor 310). The processor 310 is configurable or configured to perform, among other things, processing of information, processing of communications between elements of the surgical system 100, and control and management of elements of the surgical system 100. For example, the processor 310 is configurable or configured to receive real-time images captured by the image capturing subsystem 210. The processor 310 is also configurable or configured to receive real-time measurements (also referred to herein as IMU information) from the IMU subsystem 220.

After receiving the images and/or IMU information, the processor 310 is configurable or configured to process the images to determine whether or not the images include the scope head assembly 230 (e.g., determine whether the scope head assembly 310 is within the image capturing view of the image capturing subsystem 210). The processor 310 is also configurable or configured to process the images to determine whether or not the images include the distal end 230a of the scope head assembly 230. Such processing of images may include, cooperate with, and/or apply automated image processing and/or artificial intelligence algorithms (e.g., machine learning and/or deep learning algorithms) that receive, as inputs, images from the image capturing subsystem 210 and provide, as outputs, feature detection (i.e., identification of the distal end 230a of the scope head assembly 230 in the images). Accordingly, the processor 310 is configurable or configured to identify the distal end 230a of the scope head assembly 230 in the images. In some example embodiments, the processor 310 is also configurable or configured to generate, in the images that are to be displayed on the graphical display 304, a visible indicator for the distal end 230a of the scope head assembly 230. The processor 310 is also configurable or configured to generate real-time 3-dimensional positions (e.g., Cartesian coordinates) of the distal end 230a of the scope head assembly 230 when the processor 310 determines that the images include the distal end 230a of the scope head assembly 230. The processor 310 is also configurable or configured to generate real-time depth information for the distal end 230a of the scope head assembly 230 (e.g., depth information between the distal end 230a of the scope head assembly 230 and a reference point on the main assembly 200, such as center axis of the image capturing assembly 210).

In addition to processing of the images to identify the distal end 230a of the scope head assembly 230, the processor 310 is configurable or configured to process the images to determine whether or not the images include a cannulation target. For example, when performing an ERCP cannulation procedure, the cannulation target may be the papilla (or papillary orifice, as seen from the duodenum) that opens up into the common bile duct (CBD) and the pancreatic duct). It is to be understood that other procedures and other cannulation targets are also contemplated without departing from the teachings of the present disclosure. Such processing of images may include, cooperate with, and/or apply automated image processing and/or artificial intelligence algorithms (e.g., machine learning and/or deep learning algorithms) that receive, as inputs, images from the image capturing subsystem 210 and provide, as outputs, feature detection (i.e., identification of the cannulation target in the images). Accordingly, the processor 310 is also configurable or configured to identify the cannulation target in the images. In some example embodiments, the processor 310 is also configurable or configured to generate, in the images that are to be displayed on the graphical display 304, a visible indicator (e.g., a bounding box) for the cannulation target. The processor 310 is also configurable or configured to generate real-time 3-dimensional positions (e.g., Cartesian coordinates) of the cannulation target when the processor 310 determines that the images include the cannulation target. The processor 310 is also configurable or configured to generate real-time depth information for the cannulation target (e.g., depth information between the cannulation target and a reference point on the main assembly 200, such as center axis of the image capturing assembly 210).

When the processor 310 determines that the images include at least the distal end 230a of the scope head assembly 230, the processor 310 is configurable or configured to generate a predicted real-time trajectory path 20 for the distal end 230a of the scope head assembly 230 (i.e., generating in real-time). The processor 310 is also configurable or configured to generate a predicted real-time post-cannulation trajectory path 10 for the cannulation target when the processor 310 determines that the images include at least the cannulation target (i.e., generating in real-time). The processor 310 is also configurable or configured to generate a predicted real-time trajectory path 20 and/or predicted real-time post-cannulation trajectory path 10 for the distal end 230a of the scope head assembly 230 to cannulate the cannulation target when the processor 310 determines that the images include both the distal end 230a of the scope head assembly 230 and the cannulation target (i.e., generating in real-time). Such generating of predicted trajectory paths 10, 20 may include, cooperate with, and/or apply automated image processing, automated IMU information processing, and/or artificial intelligence algorithms (e.g., machine learning and/or deep learning algorithms) that receive, as inputs, real-time images from the image capturing subsystem 210, real-time IMU information from the IMU assembly 220, historic images from the database 330 and/or network 320, and/or historic IMU information from the database 330 and/or network 320, and provide, as outputs, the predicted trajectory path 20 and/or predicted post-cannulation trajectory path 10.

Once the predicted trajectory path 20 and/or predicted post-cannulation trajectory path 10 are generated, the processor 310 is configurable or configured to display, on a graphical display, a predicted real-time trajectory path 20 for the distal end 230a of the scope head assembly 230 when the processor 310 determines that the images include at least the distal end 230a of the scope head assembly 230 (i.e., displaying in real-time). The processor 310 is also configurable or configured to display, on a graphical display, a predicted real-time post-cannulation trajectory path 10 for the cannulation target when the processor 310 determines that the images include at least the cannulation target (i.e., displaying in real-time). The processor 310 is also configurable or configured to display, on a graphical display, a predicted real-time trajectory path 20 and/or predicted real-time post-cannulation trajectory path 10 for the distal end 230a of the scope head assembly 230 to cannulate the cannulation target when the processor 310 determines that the images include both the distal end 230a of the scope head assembly 230 and the cannulation target (i.e., displaying in real-time). The processor 310 is also configurable or configured to generate real-time depth information between the cannulation target and the distal end 230a of the scope head assembly 230 based on, among other things, the 3-dimensional positions of the distal end 230a of the scope head assembly 230 and the cannulation target.

To perform the actions, functions, processes, and/or methods described above and in the present disclosure, example embodiments of the processor 310 include one or more elements. For example, as illustrated FIG. 5A, the processor 310 includes one or more image capturing subsystem interfaces 311. The processor 310 also includes one or more IMU subsystem interfaces 312. The processor 310 also includes one or more scope head assembly processors 314. The processor 310 also includes one or more cannulation target processors 316. The processor 310 also includes one or more trajectory path processors 318.

Although the actions, functions, processes, and/or methods performed by the processor 310 may be described in the present disclosure as being performed by one or more particular elements of the processor 310, the actions, functions, processes, and/or methods performed by a particular element of the processor 310 may also be performed by one or more other elements and/or cooperatively performed by more than one element of the processor 310 (and/or other elements of the surgical system 100) without departing from the teachings of the present disclosure. It is also to be understood in the present disclosure that, although the actions, functions, processes, and/or methods performed by the processor 310 are described in the present disclosure as being performed by particular elements of the processor 310, the actions, functions, processes, and/or methods performed by two or more particular elements of the processor 310 may be combined and performed by one element of the processor 310 without departing from the teachings of the present disclosure.

These elements of the processor 310 will now be further described with reference to the accompanying figures.

The Image Capturing Subsystem Interface (e.g., Image Capturing Subsystem Interface 311).

Figure 5A:
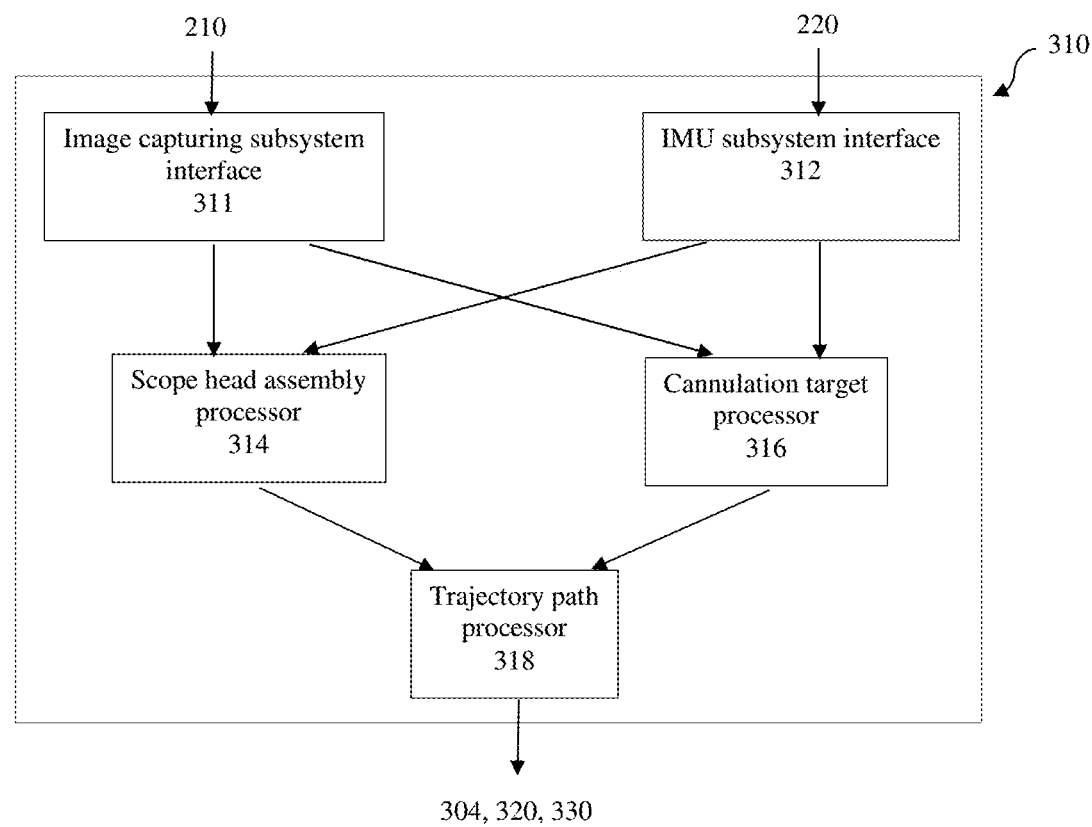
FIG. 5A is an illustration of an example embodiment of a processor of the surgical system.

As illustrated in at least FIG. 5A, the processor 310 includes one or more image capturing subsystem interfaces (e.g., image capturing subsystem interface 311). The image capturing subsystem interface 311 is configurable or configured to perform, among other things, communications with the image capturing subsystem 210. For example, the image capturing subsystem interface 311 receives real-time images captured by the image capturing subsystem 210. The image capturing subsystem interface 311 may also receive historic images captured by the image capturing subsystem 210 (and/or other surgical systems 100), such as historic images of successful procedures (e.g., successful ERCP cannulation procedures) and/or historic images of unsuccessful procedures. Such historic images may be received from the database 330 and/or network 320.

The images received by the image capturing subsystem interface 311 (including the real-time images received from the image capturing subsystem 210 and/or the historic images received from the database 330 and/or network 32) are then selectively provided or routed to the scope head assembly processor 314 and the cannulation target processor 316 for further processing.

In example embodiments, real-time images captured by the image capturing subsystem 210 may also be provided to the graphical display 304 (and the network 320 and/or database 330) in real time (i.e., in addition to (or in parallel with) providing the real-time images to the image capturing subsystem interface 311). Alternatively or in addition, real-time images captured by the image capturing subsystem 210 may be provided to the image capturing subsystem interface 311, which then selectively routes the real-time images to the graphical display 304, the network 320, the database 330, the scope head assembly processor 314, and/or the cannulation target processor 316.

The IMU Subsystem Interface (e.g., IMU Subsystem Interface 312).

As illustrated in at least FIG. 5A, the processor 310 includes one or more IMU subsystem interfaces (e.g., IMU subsystem interface 312). The IMU subsystem interface 312 is configurable or configured to perform, among other things, communications with the IMU subsystem 220. For example, the IMU subsystem interface 312 receives real-time measurements made by the IMU subsystem 220. The IMU subsystem interface 312 may also receive historic measurements made by the IMU subsystem 220 (and/or other surgical systems 100), such as historic measurements of successful procedures (e.g., successful ERCP cannulation procedures) and/or historic measurements of unsuccessful procedures. Such historic measurements may be received from the database 330 and/or network 320.

The measurements received by the IMU subsystem interface 312 (including the real-time measurements received from the IMU subsystem 220 and/or the historic measurements received from the database 330 and/or network 32) are then selectively provided or routed to the scope head assembly processor 314 and the cannulation target processor 316 for further processing.

In example embodiments, real-time measurements made by the IMU subsystem 220 may also be provided to the network 320 and/or database 330 in real time (i.e., in addition to (or in parallel with) providing the real-time measurements to the IMU subsystem interface 311). Alternatively or in addition, real-time measurements made by the IMU subsystem 220 may be provided to the IMU subsystem interface 312, which then selectively routes the real-time measurements to the network 320, the database 330, the scope head assembly processor 314, and/or the cannulation target processor 316.

It is to be understood that the image capturing subsystem interface 311 and the IMU subsystem interface 312 may be combined together as one element without departing from the teachings of the present disclosure.

The Scope Head Assembly Processor (e.g., Scope Head Assembly Processor 314).

As illustrated in at least FIG. 5A, the processor 310 includes one or more scope head assembly processors (e.g., scope head assembly processor 314). The scope head assembly processor 314 is configurable or configured to perform, among other things, processing of information pertaining to the scope head assembly 230. For example, the scope head assembly processor 314 is configurable or configured to receive real-time images, as captured by the image capturing subsystem 210, from the image capturing subsystem interface 311. The scope head assembly processor 314 is also configurable or configured to receive real-time IMU information, as measured by the IMU subsystem 220, from the IMU subsystem interface 312. The scope head assembly processor 314 is also configurable or configured to process the images to determine whether or not the images include the scope head assembly 230. In some example embodiments, the scope head assembly processor 314 is also configurable or configured to generate, in the images that are to be displayed on the graphical display 304, a visible indicator for the distal end 230a of the scope head assembly 230. The scope head assembly processor 314 is also configurable or configured to generate real-time 3-dimensional positions (e.g., Cartesian coordinates) of the distal end 230a of the scope head assembly 230 when the processor 310 determines that the images include the distal end 230a of the scope head assembly 230. The scope head assembly processor 314 is also configurable or configured to generate real-time depth information for the distal end 230a of the scope head assembly 230 (e.g., depth information between the distal end 230a of the scope head assembly 230 and a reference point on the main assembly 200, such as center axis of the image capturing assembly 210).

To perform the actions, functions, processes, and/or methods described above and in the present disclosure, example embodiments of the scope head assembly processor 314 include one or more elements. For example, as illustrated FIG. 5B, the scope head assembly processor 314 includes one or more scope head assembly detectors 314a. The scope head assembly processor 314 also includes one or more scope head assembly position generators 314b. The scope head assembly processor 314 also includes one or more scope head assembly visual indicator generators 314c.

Although the actions, functions, processes, and/or methods performed by the scope head assembly processor 314 may be described in the present disclosure as being performed by one or more particular elements of the scope head assembly processor 314, the actions, functions, processes, and/or methods performed by a particular element of the scope head assembly processor 314 may also be performed by one or more other elements and/or cooperatively performed by more than one element of the scope head assembly processor 314 (and/or other elements of processor 310 and/or the surgical system 100) without departing from the teachings of the present disclosure. It is also to be understood in the present disclosure that, although the actions, functions, processes, and/or methods performed by the scope head assembly processor 314 are described in the present disclosure as being performed by particular elements of the scope head assembly processor 314, the actions, functions, processes, and/or methods performed by two or more particular elements of the scope head assembly processor 314 may be combined and performed by one element of the scope head assembly processor 314 without departing from the teachings of the present disclosure.

These elements of the scope head assembly processor 314 will now be further described with reference to the accompanying figures.

(i) Scope Head Assembly Detector (e.g., Scope Head Assembly Detector 314a).

Figure 5B:
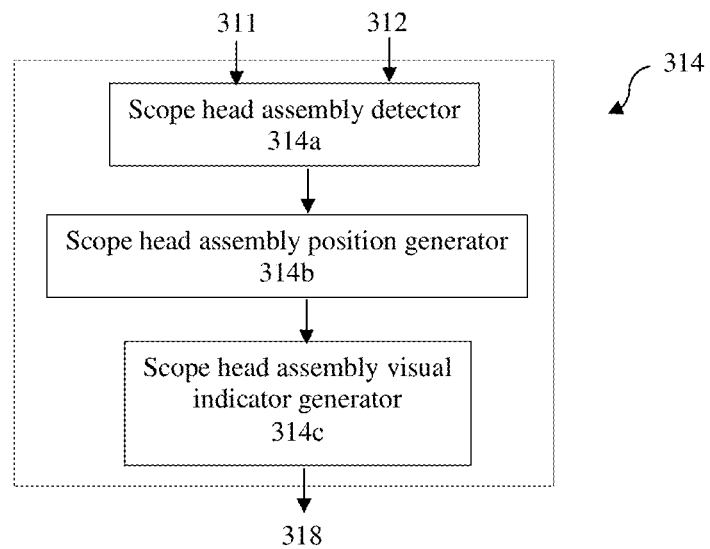
FIG. 5B is an illustration of an example embodiment of a scope head assembly processor.

As illustrated in at least FIG. 5B, the scope head assembly processor 314 includes one or more scope head assembly detectors (e.g., scope head assembly detector 314a). The scope head assembly detector 314a is configurable or configured to receive real-time images, as captured by the image capturing subsystem 210, from the image capturing subsystem interface 311. The scope head assembly detector 314a may also receive historic images captured by the image capturing subsystem 210 (and/or other surgical systems 100), such as historic images of successful procedures (e.g., successful ERCP cannulation procedures) and/or historic images of unsuccessful procedures. Such historic images may be received from the database 330 and/or network 320.

The scope head assembly detector 314a then processes the images (i.e., the real-time images, and may also process the historic images as well) to determine whether or not the images include the scope head assembly 230. More specifically, the scope head assembly detector 314*a* is configurable or configured to process the images to determine whether or not the images include the distal end 230*a* of the scope head assembly 230, and if so, where the distal end 230*a* of the scope head assembly 230 is located in the images. Put differently, the scope head assembly detector 314*a* determines whether or not the distal end 230*a* of the scope head assembly 310 is within the image capturing view of the image capturing subsystem 210, and identifies the location of the distal end 230*a* of the scope head assembly 310 within the images. Such processing by the scope head assembly detector 314*a*, including calculations, estimations, results, inferences, predictions, or the like, may be generated and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the scope head assembly detector 314*a* (and/or one or more elements of the processor 310 and/or surgical system 100) and/or via cloud computing 310, distributed computing 310, and/or non-localized or decentralized artificial intelligence (AI) 310, etc.

The scope head assembly detector 314*a* then provides the identified/located distal end 230*a* of the scope head assembly 310, as identified/located in the images, to the scope head assembly position generator 314*b* for further processing.

(ii) Scope Head Assembly Position Generator (e.g., Scope Head Assembly Position Generator 314*b*).

As illustrated in at least FIG. 5B, the scope head assembly processor 314 includes one or more scope head assembly position generators (e.g., scope head assembly position generators 314*b*). The scope head assembly position generator 314*b* is configurable or configured to receive real-time images, as captured by the image capturing subsystem 210, from the image capturing subsystem interface 311. The scope head assembly position generator 314*b* also receives processing results of the scope head assembly detector 314*a*, including the identification or location of the distal end 230*a* of the scope head assembly 310 in the received images. The scope head assembly position generator 314*b* also receives real-time IMU information, as measured by the IMU subsystem 220, from the IMU subsystem interface 312.

With the received information, the scope head assembly position generator 314*b* then generates, in real-time, 3-dimensional positions (e.g., Cartesian coordinates) of the distal end 230*a* of the scope head assembly 230. In an example embodiment, the scope head assembly position generator 314*b* generates, in real-time, a 3-dimensional position (e.g., Cartesian coordinates) of a single point of the distal end 230*a* of the scope head assembly 230, such as a most distal point of the distal end 230*a* of the scope head assembly 230. Each such 3-dimensional position of the single point of the distal end 230*a* of the scope head assembly 230 may be generated for each instance in time, which may be generated continuously, periodically (such as every 1 ms, or more or less frequent), upon the occurrence of an event (such as upon detection of movement via the IMU subsystem 220; upon detection of a movement via a change images; upon detection of a movement via a change in location of one or more points/features between images; etc.), etc. Alternatively, the scope head assembly position generator 314*b* may generate, in real-time and for each instance in time, 3-dimensional positions (e.g., Cartesian coordinates) of a plurality of points of the distal end 230*a* of the scope head assembly 230. Such plurality of 3-dimensional positions of the plurality of points of the distal end 230*a* of the scope head assembly 230 may be points or parts that make up or define a most distal edge, corner, side, etc. of the distal end 230*a* of the scope head assembly 230. Each such 3-dimensional positions of the plurality of points of the distal end 230*a* of the scope head assembly 230 may be generated for each instance in time, which may be generated continuously, periodically (such as every 1 ms, or more or less frequent), upon the occurrence of an event (such as upon detection of movement via the IMU subsystem 220; upon detection of a movement via a change images; upon detection of a movement via a change in location of one or more points/features between images; etc.), etc.

With the received information, the scope head assembly position generator 314*b* may also generate, in real-time, depth information of the distal end 230*a* of the scope head assembly 230. For example, the depth information of the distal end 230*a* of the scope head assembly 230 may be depth information identifying a depth (or distance) between the distal end 230*a* of the scope head assembly 230 and a reference point on the main assembly 200 (e.g., a center axis of the image capturing assembly 210, a center axis of the opening in the main body 200' where the scope head assembly 230 extends outwardly, etc.).

The generating of the 3-dimensional positions of the distal end 230*a* of the scope head assembly 230 (and/or depth information) by the scope head assembly position generator 314*b*, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the scope head assembly position generator 314*b* (and/or one or more elements of the processor 310 and/or surgical system 100) and/or via cloud computing 310, distributed computing 310, and/or non-localized or decentralized artificial intelligence (AI) 310, etc.

The scope head assembly position generator 314*b* then provides the 3-dimensional positions (and/or depth information) of the distal end 230*a* of the scope head assembly 310 to the scope head assembly visual indicator generator 314*c* and/or the trajectory path processor 318 for further processing. The scope head assembly position generator 314*b* may also provide the 3-dimensional positions (and/or depth information) of the distal end 230*a* of the scope head assembly 310 to the graphical display 304 for displaying to the surgeon.

(iii) Scope Head Assembly Visual Indicator Generator (e.g., Scope Head Assembly Visual Indicator Generator 314c).

As illustrated in at least FIG. 5B, the scope head assembly processor 314 includes one or more scope head assembly visual indicator generators (e.g., scope head assembly visual indicator generator 314c). The scope head assembly visual indicator generator 314c is configurable or configured to receive real-time images, as captured by the image capturing subsystem 210, from the image capturing subsystem interface 311. The scope head assembly visual indicator generator 314c also receives processing results of the scope head assembly detector 314a, including the identification or location of the distal end 230a of the scope head assembly 310 (if any is detected and identified) in the received images. The scope head assembly visual indicator generator 314c may also receive real-time IMU information, as measured by the IMU subsystem 220, from the IMU subsystem interface 312.

With the received information, the scope head assembly visual indicator generator 314c then generates, in real-time, for the images that are to be displayed on the graphical display 304, a visible indicator for the distal end 230a of the scope head assembly 230. The visible indicator may be any visible indicator including, but not limited to, a highlight, outline, symbol, bounding box, and/or the like. Such visible indicators enable the surgeon to readily identify the distal end 230a of the scope head assembly 230 when viewing the graphical display 304.

The generating of the visual indicators for the distal end 230a of the scope head assembly 230 by the scope head assembly visual indicator generator 314c, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the scope head assembly visual indicator generator 314c (and/or one or more elements of the processor 310 and/or surgical system 100) and/or via cloud computing 310, distributed computing 310, and/or non-localized or decentralized artificial intelligence (AI) 310, etc.

The scope head assembly visual indicator generator 314c then provides the visual indicators for the distal end 230a of the scope head assembly 310 to the trajectory path processor 318 for further processing. The scope head assembly visual indicator generator 314c may also provide the visual indicators for the distal end 230a of the scope head assembly 310 to the graphical display 304 for displaying to the surgeon.

The Cannulation Target Processor (e.g., Cannulation Target Processor 316).

As illustrated in at least FIG. 5A, the processor 310 includes one or more cannulation target processors (e.g., cannulation target processor 316). The cannulation target processor 316 is configurable or configured to perform, among other things, processing of information pertaining to a cannulation target (e.g., a papilla (or papillary orifice)). For example, the cannulation target processor 316 is configurable or configured to receive real-time images, as captured by the image capturing subsystem 210, from the image capturing subsystem interface 311. The cannulation target processor 316 is also configurable or configured to receive real-time IMU information, as measured by the IMU subsystem 220, from the IMU subsystem interface 312. The cannulation target processor 316 is also configurable or configured to process the images to determine whether or not the images include the cannulation target. In some example embodiments, the cannulation target processor 316 is also configurable or configured to generate, in the images that are to be displayed on the graphical display 304, a visible indicator for the cannulation target. The cannulation target processor 316 is also configurable or configured to generate real-time 3-dimensional positions (e.g., Cartesian coordinates) of the cannulation target when the processor 310 determines that the images include the cannulation target. The cannulation target processor 316 is also configurable or configured to generate real-time depth information for the cannulation target (e.g., depth information between the cannulation target and a reference point on the main assembly 200, such as center axis of the image capturing assembly 210).

To perform the actions, functions, processes, and/or methods described above and in the present disclosure, example embodiments of the cannulation target processor 316 include one or more elements. For example, as illustrated FIG. 5C, the cannulation target processor 316 includes one or more cannulation target detectors 316a. The cannulation target processor 316 also includes one or more cannulation target position generators 316b. The cannulation target processor 316 also includes one or more cannulation target visual indicator generators 316c.

Although the actions, functions, processes, and/or methods performed by the cannulation target processor 316 may be described in the present disclosure as being performed by one or more particular elements of the cannulation target processor 316, the actions, functions, processes, and/or methods performed by a particular element of the cannulation target processor 316 may also be performed by one or more other elements and/or cooperatively performed by more than one element of the cannulation target processor 316 (and/or other elements of processor 310 and/or the surgical system 100) without departing from the teachings of the present disclosure. It is also to be understood in the present disclosure that, although the actions, functions, processes, and/or methods performed by the cannulation target processor 316 are described in the present disclosure as being performed by particular elements of the cannulation target processor 316, the actions, functions, processes, and/or methods performed by two or more particular elements of the cannulation target processor 316 may be combined and performed by one element of the cannulation target processor 316 without departing from the teachings of the present disclosure. It is also to be understood that the scope head assembly processor 314 (or one or more elements of the scope head assembly processor 314) and the cannulation target processor 316 (or one or more elements of the cannulation target processor 316) may be combined together as one processor without departing from the teachings of the present disclosure.

These elements of the scope head assembly processor 314 will now be further described with reference to the accompanying figures.

(i) Cannulation Target Detector (e.g., Cannulation Target Detector 316a).

Figure 5C:
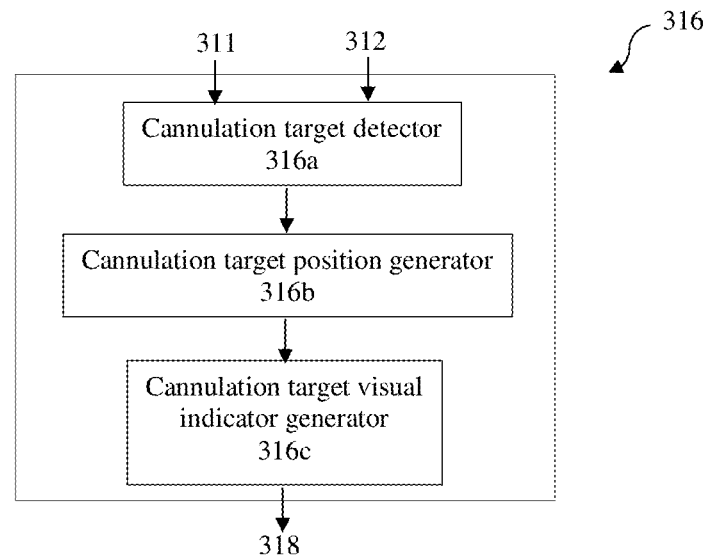
FIG. 5C is an illustration of an example embodiment of a cannulation target processor.

As illustrated in at least FIG. 5C, the cannulation target processor 316 includes one or more cannulation target detectors (e.g., cannulation target detector 316a). The cannulation target detector 316a is configurable or configured to receive real-time images, as captured by the image capturing subsystem 210, from the image capturing subsystem interface 311. The cannulation target detector 316a may also receive historic images captured by the image capturing subsystem 210 (and/or other surgical systems 100), such as historic images of successful procedures (e.g., successful ERCP cannulation procedures) and/or historic images of unsuccessful procedures. Such historic images may be received from the database 330 and/or network 320.

The cannulation target detector 316a then processes the images (i.e., the real-time images, and may also process the historic images as well) to determine whether or not the images include a cannulation target, and if so, where the cannulation target is located in the images. Put differently, the cannulation target detector 316a determines whether or not the cannulation target is within the image capturing view of the image capturing subsystem 210, and identifies the location of the cannulation target within the images. Such processing by the cannulation target detector 316a, including calculations, estimations, results, inferences, predictions, or the like, may be generated and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the cannulation target detector 316a (and/or one or more elements of the processor 310 and/or surgical system 100) and/or via cloud computing 310, distributed computing 310, and/or non-localized or decentralized artificial intelligence (AI) 310, etc.

The cannulation target detector 316a then provides the identified/located cannulation target, as identified/located in the images, to the cannulation target position generator 316b for further processing.

(ii) Cannulation Target Position Generator (e.g., Cannulation Target Position Generator 316b).

As illustrated in at least FIG. 5C, the cannulation target processor 316 includes one or more cannulation target position generators (e.g., cannulation target position generator 316b). The cannulation target position generator 316b is configurable or configured to receive real-time images, as captured by the image capturing subsystem 210, from the image capturing subsystem interface 311. The cannulation target position generator 316b also receives processing results of the cannulation target detector 316a, including the identification or location of the cannulation target (if any is detected and identified) in the received images. The cannulation target position generator 316b also receives real-time IMU information, as measured by the IMU subsystem 220, from the IMU subsystem interface 312.

With the received information, the cannulation target position generator 316b then generates, in real-time, 3-dimensional positions (e.g., Cartesian coordinates) of the cannulation target. In an example embodiment, the cannulation target position generator 316b generates, in real-time, a 3-dimensional position (e.g., Cartesian coordinates) of a single point of the cannulation target, such as a center point of the cannulation target (e.g., when the cannulation target is a papilla orifice, the single point may be a center point of the papilla orifice). Each such 3-dimensional position of the single point of the cannulation target may be generated for each instance in time, which may be generated continuously, periodically (such as every 1 ms, or more or less frequent), upon the occurrence of an event (such as upon detection of movement via the IMU subsystem 220; upon detection of a movement via a change images; upon detection of a movement via a change in location of one or more points/features between images; etc.), etc. Alternatively, the cannulation target position generator 316b may generate, in real-time and for each instance in time, 3-dimensional positions (e.g., Cartesian coordinates) of a plurality of points of the cannulation target. Such plurality of 3-dimensional positions of the plurality of points of the cannulation target may be points or parts that make up or define edges, peripherals, sides, etc. of the cannulation target. Each such 3-dimensional positions of the plurality of points of the cannulation target may be generated for each instance in time, which may be generated continuously, periodically (such as every 1 ms, or more or less frequent), upon the occurrence of an event (such as upon detection of movement via the IMU subsystem 220; upon detection of a movement via a change images; upon detection of a movement via a change in location of one or more points/features between images; etc.), etc.

With the received information, the cannulation target position generator 316b may also generate, in real-time, depth information of the cannulation target. For example, the depth information of the cannulation target may be depth information identifying a depth (or distance) between the cannulation target and a reference point on the main assembly 200 (e.g., a center axis of the image capturing assembly 210, a center axis of the opening in the main body 200' where the scope head assembly 230 extends outwardly, etc.).

The generating of the 3-dimensional positions of the cannulation target (and/or depth information) by the cannulation target position generator 316b, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the cannulation target position generator 316b (and/or one or more elements of the processor 310 and/or surgical system 100) and/or via cloud computing 310, distributed computing 310, and/or non-localized or decentralized artificial intelligence (AI) 310, etc.

The cannulation target position generator 316b then provides the 3-dimensional positions (and/or depth information) of the cannulation target to the cannulation target visual indicator generator 316c and/or the trajectory path processor 318 for further processing. The cannulation target position generator 316b may also provide the 3-dimensional positions (and/or depth information) of the cannulation target to the graphical display 304 for displaying to the surgeon.

(iii) Cannulation Target Visual Indicator Generator (e.g., Cannulation Target Visual Indicator Generator 316c).

As illustrated in at least FIG. 5C, the cannulation target processor 316 includes one or more cannulation target visual indicator generators (e.g., cannulation target visual indicator generator 316c). The cannulation target visual indicator generator 316c is configurable or configured to receive real-time images, as captured by the image capturing subsystem 210, from the image capturing subsystem interface 311. The cannulation target visual indicator generator 316c also receives processing results of the cannulation target detector 316a, including the identification or location of the cannulation target (if any is detected and identified) in the received images. The cannulation target visual indicator generator 316c may also receive real-time IMU information, as measured by the IMU subsystem 220, from the IMU subsystem interface 312.

With the received information, the cannulation target visual indicator generator 316c then generates, in real-time, for the images that are to be displayed on the graphical display 304, a visible indicator for the cannulation target. The visible indicator may be any visible indicator including, but not limited to, a highlight, outline, symbol, bounding box, and/or the like. Such visible indicators enable the surgeon to readily identify the cannulation target when viewing the graphical display 304.

The generating of the visual indicators for the cannulation target by the cannulation target visual indicator generator 316c, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the cannulation target visual indicator generator 316c (and/or one or more elements of the processor 310 and/or surgical system 100) and/or via cloud computing 310, distributed computing 310, and/or non-localized or decentralized artificial intelligence (AI) 310, etc.

The cannulation target visual indicator generator 316c then provides the visual indicators for the cannulation target to the trajectory path processor 318 for further processing. The cannulation target visual indicator generator 316c may also provide the visual indicators for the cannulation target to the graphical display 304 for displaying to the surgeon.

The Trajectory Path Processor (e.g., Trajectory Path Processor 318).

As illustrated in at least FIG. 5A, the processor 310 includes one or more trajectory path processors (e.g., trajectory path processor 318). The trajectory path processor 318 is configurable or configured to receive real-time images, as captured by the image capturing subsystem 210, from the image capturing subsystem interface 311. The trajectory path processor 318 may also receive historic images captured by the image capturing subsystem 210 (and/or other surgical systems 100), such as historic images of successful procedures (e.g., successful bile duct cannulation procedures) and/or historic images of unsuccessful procedures. Such historic images may be received from the database 330 and/or network 320. The trajectory path processor 318 may also receive real-time IMU information, as measured by the IMU subsystem 220, from the IMU subsystem interface 312. The trajectory path processor 318 may also receive historic measurements made by the IMU subsystem 220 (and/or other surgical systems 100), such as historic measurements (including 3-dimensional positions, orientations, accelerations, etc. for the distal end 230a of the scope head assembly 230 and/or the cannulation target) of successful procedures (e.g., successful ERCP cannulation procedures) and/or historic 3-dimensional positions (including 3-dimensional positions, orientations, accelerations, etc. for the distal end 230a of the scope head assembly 230 and/or the cannulation target) of unsuccessful procedures. Such historic measurements may be received from the database 330 and/or network 320. The trajectory path processor 318 may also receive processing results of the scope head assembly target detector 314a. The trajectory path processor 318 may also receive processing results of the scope head assembly position generator 314b. The trajectory path processor 318 may also receive processing results of the scope head assembly visual indicator generator 314c. The trajectory path processor 318 may also receive processing results of the cannulation target detector 316a. The trajectory path processor 318 may also receive processing results of the cannulation target position generator 316b. The trajectory path processor 318 may also receive processing results of the cannulation target visual indicator generator 316c.

Figure 6A:
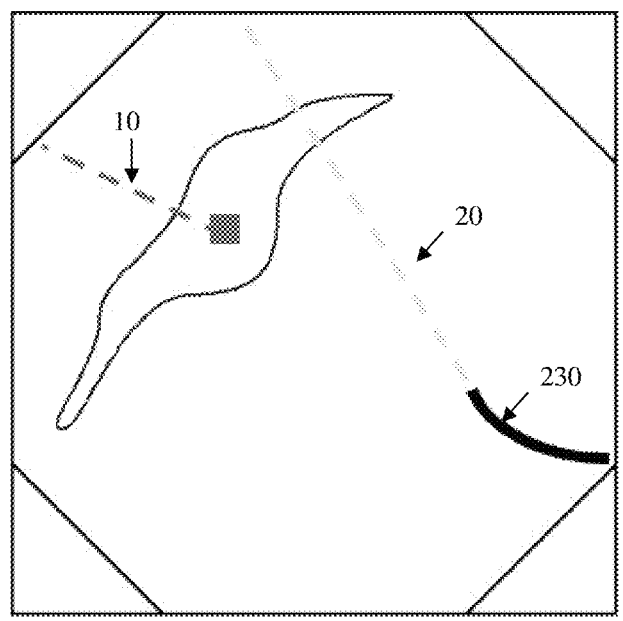
FIG. 6A is an illustration of a camera view of the image capturing assembly depicting a cannulation target, scope head assembly, predicted trajectory path, and post-cannulation predicted trajectory path.
Figure 6B:
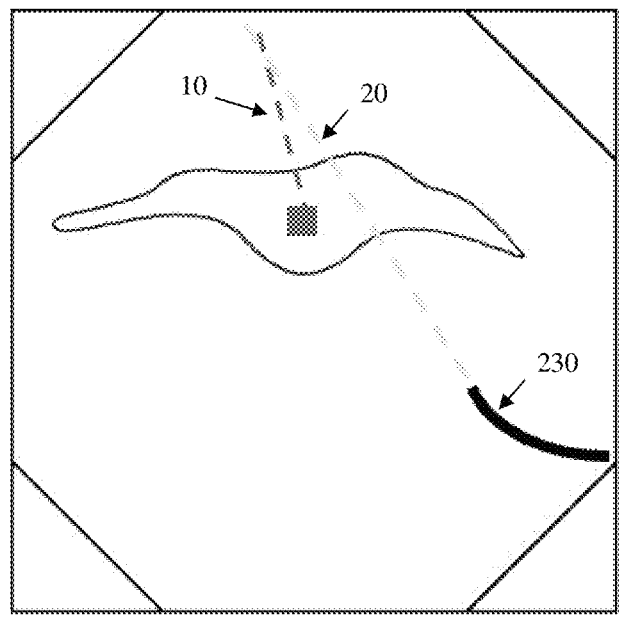
FIG. 6B is another illustration of a camera view of the image capturing assembly depicting a cannulation target, scope head assembly, predicted trajectory path, and post-cannulation predicted trajectory path.
Figure 6C:
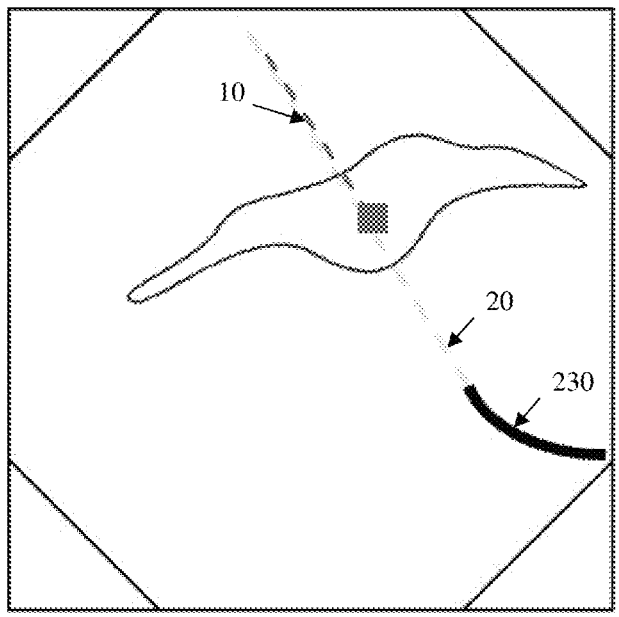
FIG. 6C is another illustration of a camera view of the image capturing assembly depicting a cannulation target, a scope head assembly positioned in an ideal position and/or orientation, a post-cannulation predicted trajectory path, and a predicted trajectory path aligned with the post-cannulation predicted trajectory path.

When the trajectory path processor 318 determines that the received images include at least the cannulation target, the trajectory path processor 318 generates, in real time, one or more post-cannulation predicted trajectory paths 10, 20 for the cannulation target. For example, as illustrated in FIG. 6A, FIG. 6B, and FIG. 6C, when performing an ERCP cannulation procedure (for the common bile duct, or CBD), the post-cannulation predicted trajectory path 10 (or bile duct orientation 10 or papillar plane 10) is the predicted trajectory path for the scope head assembly 230 to successfully reach the CBD after passing through the papillary orifice.

When the trajectory path processor 318 determines that the received images include at least the distal end 230a of the scope head assembly 230, the trajectory path processor 318 generates, in real time, one or more predicted trajectory paths for the distal end 230a of the scope head assembly 230. For example, as illustrated in FIGS. 6A-6C, when performing an ERCP cannulation procedure (for the common bile duct, or CBD), the predicted trajectory path 20 is the predicted trajectory path of the scope head assembly 230 based on, among other things, the current position and orientation of the main assembly 200 (and scope head assembly 230).

When the trajectory path processor 318 determines that the received images include both the distal end 230a of the scope head assembly 230 and the cannulation target, the trajectory path processor 318 generates, in real time, one or more predicted trajectory paths between the distal end 230a of the scope head assembly 230 and the cannulation target (i.e., one or more predicted real-time trajectory paths for the distal end 230a of the scope head assembly 230 to cannulate the cannulation target). For example, as illustrated in FIGS. 6A-6C, when performing a cannulation procedure (for the common bile duct, or CBD), the predicted trajectory path 20 is the predicted trajectory path of the scope head assembly 230 based on, among other things, the current position and orientation of the main assembly 200 (and scope head assembly 230).

When the trajectory path processor 318 determines that the received images include both the distal end 230a of the scope head assembly 230 and the cannulation target, the trajectory path processor 318 may also generate real-time depth information between the cannulation target and the distal end 230a of the scope head assembly 230.

As an illustrative example, FIG. 6A illustrates an example when the trajectory path processor 318 determines that both the distal end 230a of the scope head assembly 230 and the cannulation target are in the camera view of the image capturing assembly 210 (i.e., are identified in the received real-time image). The trajectory path processor 318 then generates, in real time, a predicted trajectory path 20 for the distal end 230a of the scope head assembly 230 based on information received, in real time, by the trajectory path processor 318, as described above and in the present disclosure. The trajectory path processor 318 also generates, in real time, a post-cannulation predicted trajectory path 10 for the cannulation target based on information received, in real time, by the trajectory path processor 318, as described above and in the present disclosure. The trajectory path processor 318 then processes the predicted trajectory path 20 and the post-cannulation predicted trajectory path 10, including comparing the paths 10, 20. In this particular example, the trajectory path processor 318 determines that the main assembly 200 (and the scope head assembly 230) are not in the ideal position and/or orientation to perform a successful ERCP cannulation procedure. In an example embodiment, the trajectory path processor 318 may (or may not) perform one or more actions as a result, including, but not limited to: providing a visual indication on the graphical display 304 that the main assembly 200 (and the scope head assembly 230) are not yet in an ideal position and/or orientation; providing recommendations, guidance, and/or visual directions for the surgeon to re-position or move the main assembly 200 (and the scope head assembly 230) toward an ideal position and/or orientation; preventing or locking the scope head assembly 230 so as to not allow the scope head assembly 230 to extend outwardly to perform the ERCP cannulation; etc. FIG. 6B illustrates an example of the surgeon moving the main assembly (and the scope head assembly 230) towards the ideal position and/or orientation (which may also be performed by trying to align the predicted trajectory path 20 for the distal end 230a of the scope head assembly 230 with the post-cannulation predicted trajectory path 10 for the cannulation target). As illustrated in FIG. 6C, the main assembly (and the scope head assembly 230) has moved to the ideal position and orientation, which can be readily identified by the surgeon based on the alignment and/or overlapping of the predicted trajectory path 20 for the distal end 230a of the scope head assembly 230 with the post-cannulation predicted trajectory path 10 for the cannulation target.

The generating of the predicted trajectory paths 20 and post-cannulation trajectory paths 10 by the trajectory path processor 318, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally via the trajectory path processor 318 (and/or one or more elements of the processor 310 and/or surgical system 100) and/or via cloud computing 310, distributed computing 310, and/or non-localized or decentralized artificial intelligence (AI) 310, etc.

The trajectory path processor 318 then provides the predicted trajectory paths 20 and/or post-cannulation trajectory paths 10 to the graphical display 304 for displaying to the surgeon. The trajectory path processor 318 may also provide the predicted trajectory paths 20 and/or post-cannulation trajectory paths 10 to the network 320 and/or database 330.

Example Embodiments of a Method of Configuring a Surgical System (e.g., Method 700).

Figure 7A:
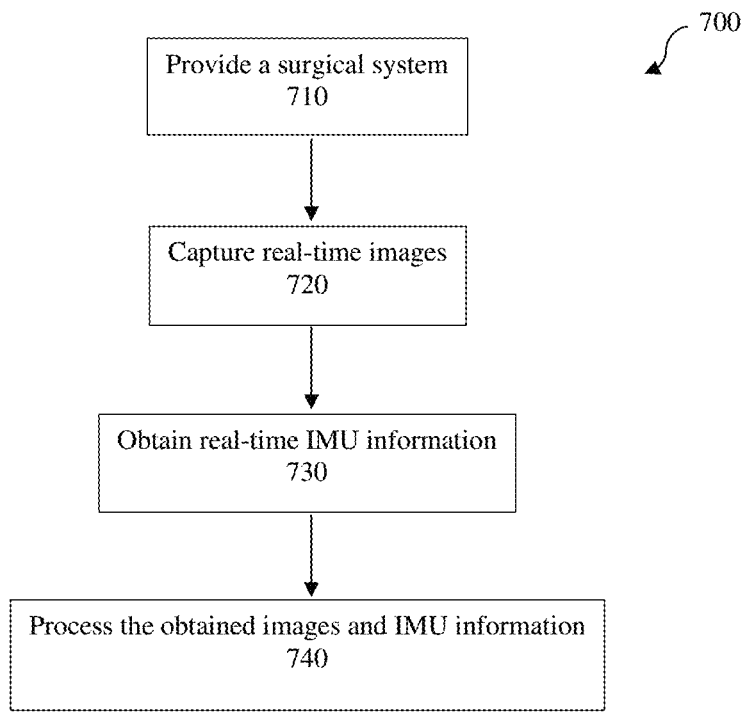
FIG. 7A is an illustration of an example embodiment of a method of configuring a surgical system.

An example embodiment of a method (e.g., method 700) of configuring a surgical system is illustrated in FIG. 7A. The method 700 includes providing a surgical system (e.g., surgical system 100, as illustrated in at least FIG. 1A) (e.g., action 710). The method 700 also includes capturing real-time images (e.g., action 720). The method 700 also includes obtaining real-time IMU information (e.g., action 730). The method 700 also includes processing the obtained images and IMU information (e.g., action 740).

These and other processes and/or actions of the method 700 will now be further described with reference to the accompanying figures.

Providing a Surgical System (e.g., Action 710).

Figure 2A:
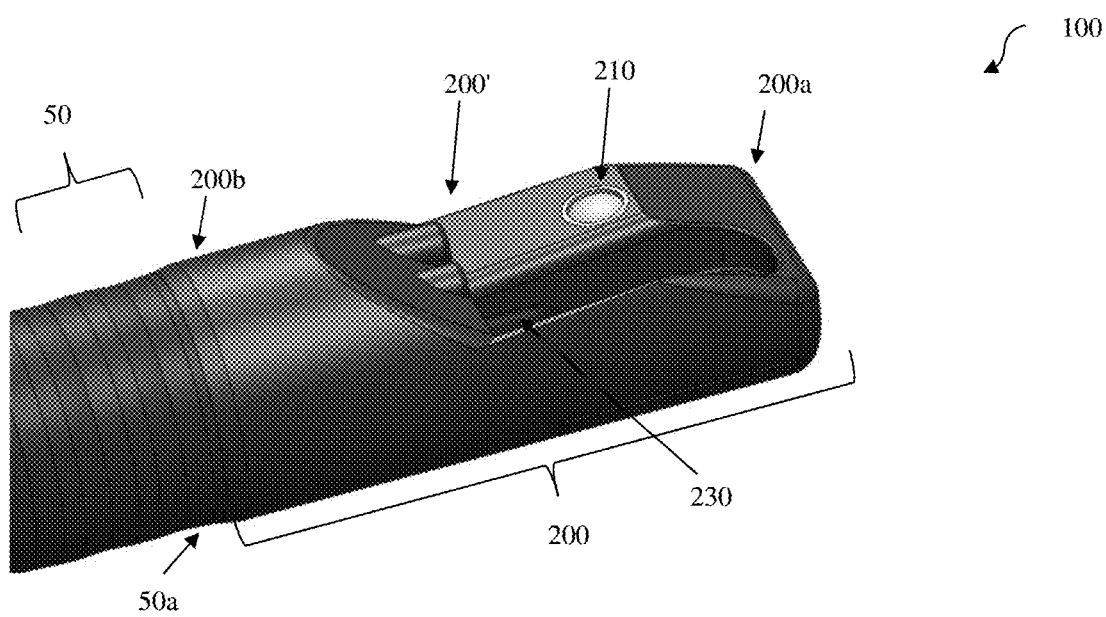
FIG. 2A is an illustration of a perspective view of an example embodiment of a main assembly of the surgical system.
Figure 2B:
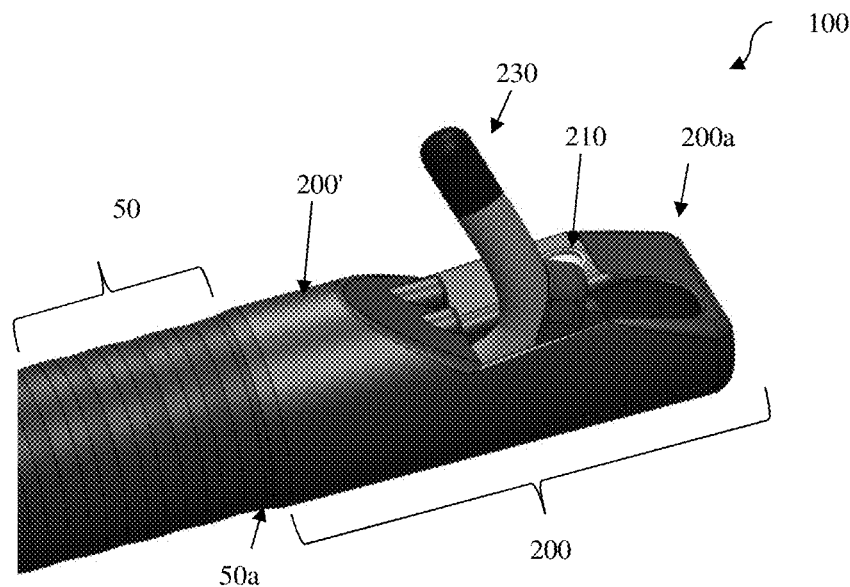
FIG. 2B is another illustration of a perspective view of an example embodiment of a main assembly with a scope head assembly extended outward from a main body of the main assembly.
Figure 2C:
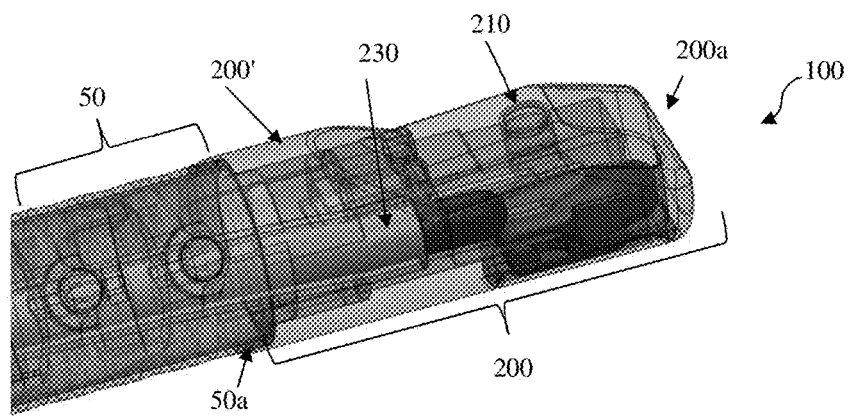
FIG. 2C is an illustration of a transparent perspective view of an example embodiment of a main body.
Figure 2D:
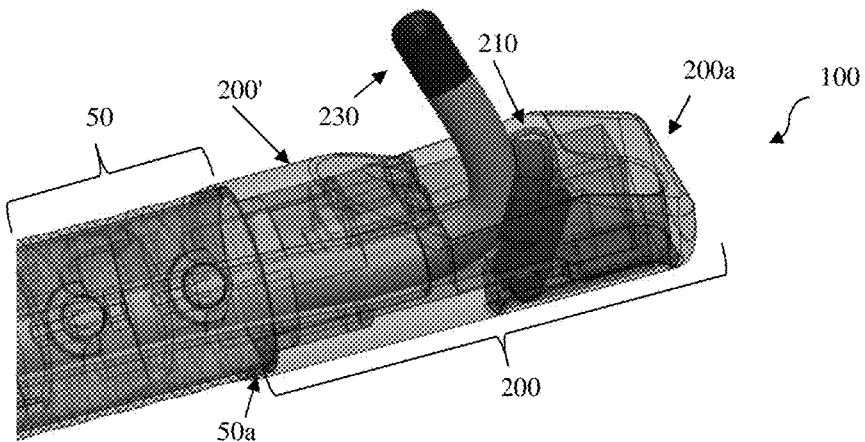
FIG. 2D is another illustration of a transparent perspective view of an example embodiment of a main assembly with a scope head assembly extended outward from a main body of the main assembly.
Figure 3A:
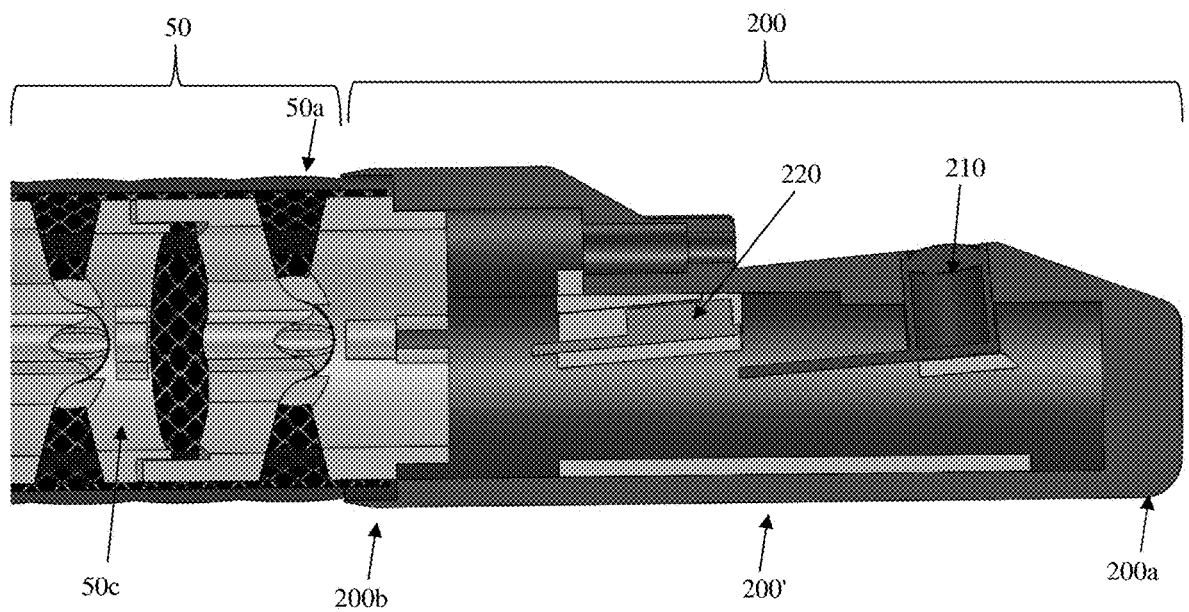
FIG. 3A is an illustration of a cross-sectional view of an example embodiment of a main assembly illustrating an image capturing assembly and an IMU assembly.
Figure 3B:
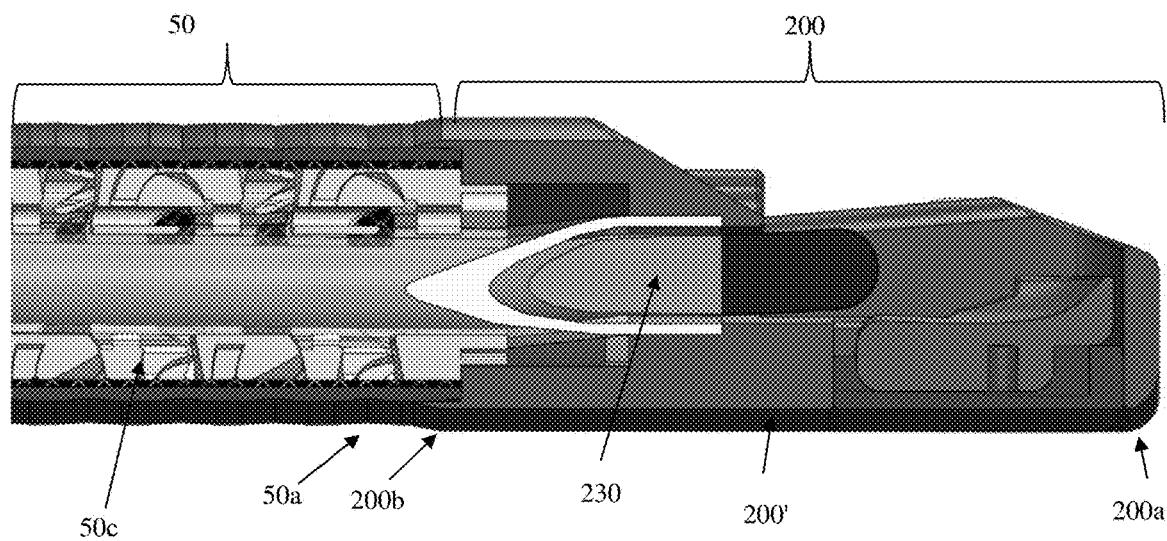
FIG. 3B is an illustration of another cross-sectional view of an example embodiment of a main assembly illustrating a scope head assembly.
Figure 3C:
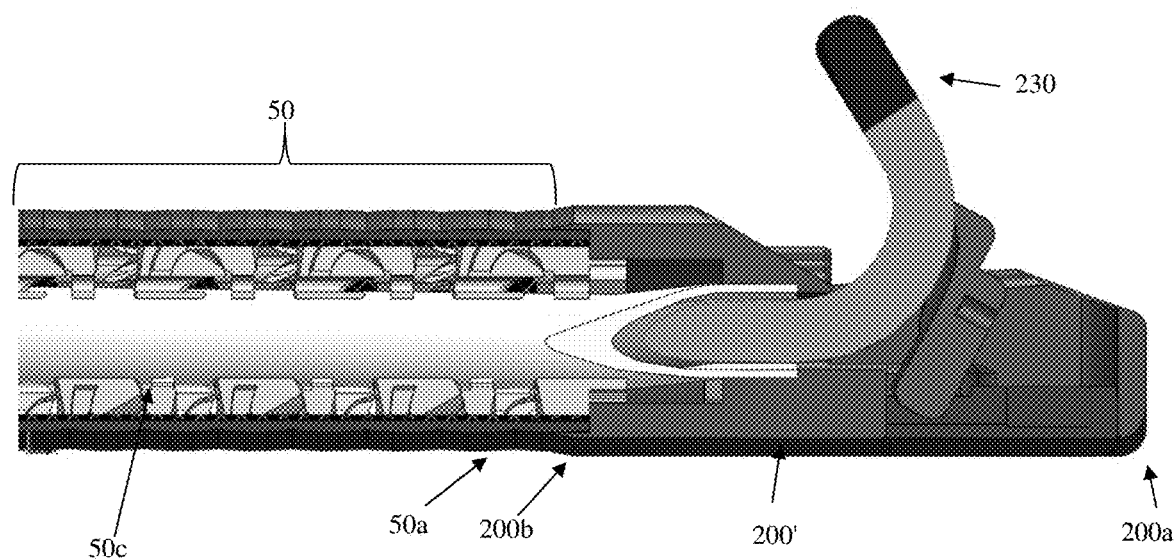
FIG. 3C is an illustration of another cross-sectional view of an example embodiment of a main assembly illustrating a scope head assembly extended outward from a main body of the main assembly.

In an example embodiment, the method 700 includes providing a surgical system (e.g., action 710). The surgical system 100 includes a main body (e.g., main body 200', as illustrated in at least FIG. 2A and described in the present disclosure). The surgical system 100 also includes one or more inertial measurement unit (IMU) subsystems (e.g., IMU subsystem 220, as illustrated in at least FIG. 3A and described in the present disclosure). The IMU subsystem 220 is housed in the main body 200' of the main assembly 200. The surgical system 100 also includes one or more image capturing subsystems 210 (e.g., image capturing subsystem 210, as illustrated in at least FIG. 2A and described in the present disclosure). The image capturing subsystem 210 is housed in the main body 200' of the main assembly 200. The surgical system 100 also includes one or more scope head assemblies (e.g., scope head assembly 230, as illustrated in at least FIG. 2B and described in the present disclosure). The scope head assembly 230 includes a proximal end and a distal end 230a. The scope head assembly 230 is configurable or configured to selectively extend the distal end 230a of the scope head assembly 230 outward from the main body 200' (e.g., as illustrated in FIG. 2B). The scope head assembly 230 (i.e., the portion that extends away from the main body 200') may be selectively varied in length (distance), bending angle, bending direction, and bending location (along the scope head assembly 230) so as to enable a surgeon to follow any predicted trajectory path 20 (as described in the present disclosure) and/or post-cannulation predicted trajectory path 10 (as described in the present disclosure).

Capturing Real-Time Images (e.g., Action 720).

As illustrated in FIG. 7A, the method 700 includes capturing of real-time images (e.g., action 720). The captured images may be video images and/or still images. Such images may be captured by example embodiments of the image capturing assembly 210, and provided in real-time to the processor (e.g., processor 310). More specifically, the images may be provided to the image capturing subsystem interface (e.g., image capturing subsystem interface 311, as illustrated in at least FIG. 5A). The images may also be provided in real-time, directly or indirectly, to the graphical display (e.g., graphical display 304) for displaying to the surgeon. The images may also be provided in real-time, directly or indirectly, to the network (e.g., network 320) and/or database (e.g., database 330).

In an example embodiment, the captured images may be provided to the processor 310 (i.e., the image capturing subsystem interface 311), which provides the captured images to the graphical display 304 to display to the surgeon; and provides the captured images to the database 330 for storing. The processor 310 then performs the processing of the images (e.g., action 740). In example embodiments where the processing of the images (e.g., action 740) is not performed entirely by a local processor 310 (e.g., in part or in whole by cloud computing 310, distributed computing 310, and/or non-localized or decentralized artificial intelligence (AI) 310, etc.), the processor 310 provides the captured images to the network 320 (which includes and/or is in communication with cloud computing 310, distributed computing 310, and/or non-localized or decentralized artificial intelligence (AI) 310, etc.) for further processing.

Obtaining Real-Time IMU Information (e.g., Action 730).

As illustrated in FIG. 7A, the method 700 includes obtaining of real-time IMU information (e.g., action 730). The obtained IMU information may include specific force, angular rate, position, and/or orientation. Such IMU information may be measured or captured by example embodiments of the IMU assembly 220 (which may include accelerometers, gyroscopes, and/or magnetometers), and provided in real-time to the processor 310. More specifically, the IMU information may be provided to the IMU subsystem interface (e.g., IMU subsystem interface 312, as illustrated in at least FIG. 5A). The IMU information may also be provided in real-time, directly or indirectly, to the graphical display 304 for displaying to the surgeon. The IMU information may also be provided in real-time, directly or indirectly, to the network 320 and/or database 330.

In an example embodiment, the IMU information may be provided to the processor 310 (i.e., the IMU subsystem interface 312), which provides the IMU information to the graphical display 304 to display to the surgeon; and provides the IMU information to the database 330 for storing. The processor 310 then performs the processing of the IMU information (e.g., action 740). In example embodiments where the processing of the IMU information (e.g., action 740) is not performed entirely by a local processor 310 (e.g., in part or in whole by cloud computing 310, distributed computing 310, and/or non-localized or decentralized artificial intelligence (AI) 310, etc.), the processor 310 provides the IMU information to the network 320 (which includes and/or is in communication with cloud computing 310, distributed computing 310, and/or non-localized or decentralized artificial intelligence (AI) 310, etc.) for further processing.

Processing the Obtained Images and IMU Information (e.g., Action 740).

Figure 7B:
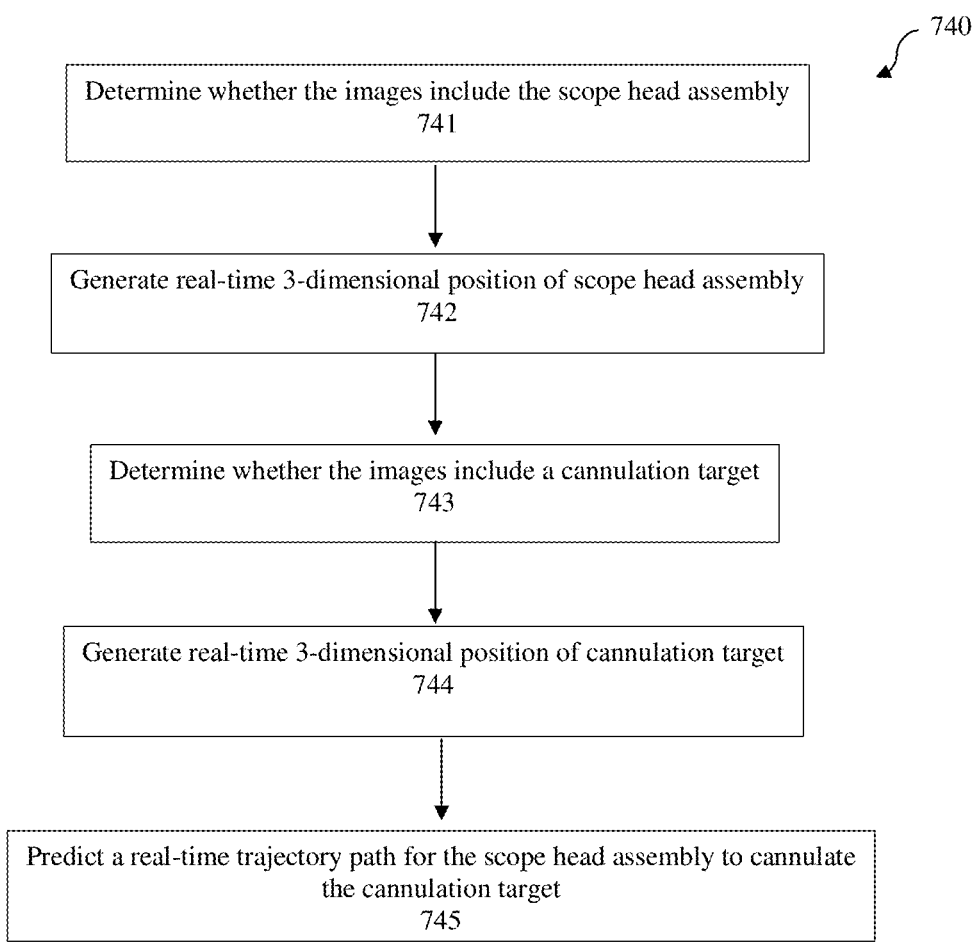
FIG. 7B is an illustration of an example embodiment of a method of processing obtained images and IMU information.

As illustrated in FIG. 7A and FIG. 7B, the method 700 includes processing of the images and IMU information (e.g., action 740). The processing 740 includes determining whether or not the images include the scope head assembly 230 (e.g., action 741). More specifically, the processing 740 includes determining whether or not the images include a distal end 230a of the scope head assembly 230 (e.g., action 741). The determining of whether or not the images include the distal end 230a of the scope head assembly 230 may include processing of historic images captured by the image capturing subsystem 210 (and/or other surgical systems 100), such as historic images of successful procedures (e.g., successful bile duct cannulation procedures) and/or historic images of unsuccessful procedures. Such historic images may be received from the database 330 and/or network 320. Such processing to determine whether or not the images include the distal end 230a of the scope head assembly 230, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally (e.g., via the scope head assembly detector 314a and/or one or more elements of the processor 310 and/or surgical system 100) and/or via cloud computing 310, distributed computing 310, and/or non-localized or decentralized artificial intelligence (AI) 310, etc.

When the processing 740 determines that the images include the distal end 230a of the scope head assembly 230, the processing 740 includes identifying the distal end 230a of the scope head assembly 230 in the images. Furthermore, when the processing 740 determines that the images include the distal end 230a of the scope head assembly 230, the processing 740 includes generating real-time 3-dimensional positions of the distal end 230a of the scope head assembly 230 (e.g., action 742). The generating of the real-time 3-dimensional positions of the distal end 230a of the scope head assembly 230 may be performed based on at least the obtained IMU information. The generating of the real-time 3-dimensional positions of the distal end 230a of the scope head assembly 230 may also be based on the obtained images. Such generating of the 3-dimensional positions of the distal end 230a of the scope head assembly 230, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally (e.g., via the scope head assembly position generator 314b and/or one or more elements of the processor 310 and/or surgical system 100) and/or via cloud computing 310, distributed computing 310, and/or non-localized or decentralized artificial intelligence (AI) 310, etc.

The processing 740 also includes determining whether or not the images include a cannulation target (e.g., a papilla or papillary orifice) (e.g., action 743). The determining of whether or not the images include the cannulation target may include processing of historic images captured by the image capturing subsystem 210 (and/or other surgical systems 100), such as historic images of successful procedures (e.g., successful bile duct cannulation procedures) and/or historic images of unsuccessful procedures. Such historic images may be received from the database 330 and/or network 320. Such processing to determine whether or not the images include the cannulation target, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally (e.g., via the cannulation target detector 316a and/or one or more elements of the processor 310 and/or surgical system 100) and/or via cloud computing 310, distributed computing 310, and/or non-localized or decentralized artificial intelligence (AI) 310, etc.

When the processing 740 determines that the images include the cannulation target, the processing 740 includes identifying the cannulation target in the images. Furthermore, when the processing 740 determines that the images include the cannulation target, the processing 740 includes generating real-time 3-dimensional positions of the cannulation target (e.g., action 744). The generating of the real-time 3-dimensional positions of the cannulation target may be performed based on at least the obtained IMU information. The generating of the real-time 3-dimensional positions of the cannulation target may also be based on the obtained images. Such generating of the 3-dimensional positions of the cannulation target, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally (e.g., via the cannulation target position generator 316b and/or one or more elements of the processor 310 and/or surgical system 100) and/or via cloud computing 310, distributed computing 310, and/or non-localized or decentralized artificial intelligence (AI) 310, etc.

When the processing 740 determines that the images include at least the distal end 230a of the scope head assembly 230, the processing 740 includes predicting one or more trajectory paths 20 of the distal end 230a of the scope head assembly 230. When the processing 740 determines that the images include at least the cannulation target, the processing 740 includes predicting one or more post-cannulation trajectory paths 10 (as described in the present disclosure). When the processing 740 determines that the images include the distal end 230a of the scope head assembly 230 and the cannulation target, the processing 740 includes predicting one or more trajectory paths for the distal end 230a of the scope head assembly 230 to cannulate the cannulation target (e.g., action 745), including predicting trajectory paths 20 and post-cannulation trajectory paths 10. Such predicting may be performed based on at least the 3-dimensional position of the distal end 230a of the scope head assembly 230 and the 3-dimensional position of the cannulation target. Furthermore, such predicting of the trajectory paths 20 and post-cannulation trajectory paths 10, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), convolutional neural networks (CNN), regional convolutional neural networks (R-CNN), Simultaneous Localization and Mapping (SLAM), etc. Furthermore, such artificial intelligence (AI) algorithms, engines, systems, processors, and/or processes may be provided locally (e.g., via the trajectory path processor 318 and/or one or more elements of the processor 310 and/or surgical system 100) and/or via cloud computing 310, distributed computing 310, and/or non-localized or decentralized artificial intelligence (AI) 310, etc.

After performing the predictions described above and in the present disclosure, the processing 740 includes generating, on the images displayed on the graphical display 304, the predicted trajectory paths 20 of the distal end 230a of the scope head assembly 230 (e.g., based on the position and/or orientation of the distal end 230a and/or other parts of the scope head assembly 230). The processing 740 also includes generating, on the images displayed on the graphical display 304, the post-cannulation predicted trajectory paths 10 when the images include the cannulation target. The processing 740 also includes generating, on the images displayed on the graphical display 304, the predicted trajectory path 20 for the distal end 230a of the scope head assembly 230 to cannulate the identified cannulation target when the images include the distal end 230a of the scope head assembly 230 and the cannulation target. Such generating of the trajectory paths 20 and post-cannulation trajectory paths 10, including calculations, estimations, results, inferences, predictions, or the like, may be performed and/or derived, directly or indirectly, partially or in whole, via artificial intelligence (AI) algorithms, engines, systems, processors, and/or processes. Such artificial intelligence (AI) algorithms, engines, systems, processors, and/or processes may include, but are not limited to, machine learning algorithms, deep learning algorithms, deep neural networks (DNN), recurrent neural networks (RNN), long short term memory (LSTM), Simultaneous Localization and Mapping (SLAM), convolutional neural networks (CNN), regional convolutional neural networks (R-CNN), etc. Furthermore, such artificial intelligence (AI) algorithms, engines, systems, processors, and/or processes may be provided locally (e.g., via the trajectory path processor 318 and/or one or more elements of the processor 310 and/or surgical system 100) and/or via cloud computing 310, distributed computing 310, and/or non-localized or decentralized artificial intelligence (AI) 310, etc.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "communication," "communicate," "connection," "connect," or other similar terms should generally be construed broadly to mean a wired, wireless, and/or other form of, as applicable, connection between elements, devices, computing devices, telephones, processors, controllers, servers, networks, telephone networks, the cloud, and/or the like, which enable voice and/or data to be sent, transmitted, broadcasted, received, intercepted, acquired, and/or transferred (each as applicable).

As another example, "user," "operator," "surgeon," or similar terms should generally be construed broadly to mean a user who is operating, controlling, managing, or the like, one or more elements of the surgical system (e.g., surgical system 100) and/or processor (e.g., processor 310).

Also, as referred to herein, a processor, device, computing device, telephone, phone, server, gateway server, communication gateway server, and/or controller, may be any processor, computing device, and/or communication device, and may include a virtual machine, computer, node, instance, host, or machine in a networked computing environment. Also as referred to herein, a network or cloud may be or include a collection of machines connected by communication channels that facilitate communications between machines and allow for machines to share resources. Network may also refer to a communication medium between processes on the same machine. Also as referred to herein, a network element, node, or server may be a machine deployed to execute a program operating as a socket listener and may include software instances.

Database (or memory or storage) may comprise any collection and/or arrangement of volatile and/or non-volatile components suitable for storing data. For example, memory may comprise random access memory (RAM) devices, read-only memory (ROM) devices, magnetic storage devices, optical storage devices, solid state devices, and/or any other suitable data storage devices. In particular embodiments, database may represent, in part, computer-readable storage media on which computer instructions and/or logic are encoded. Database may represent any number of memory components within, local to, and/or accessible by a processor and/or computing device.

Various terms used herein have special meanings within the present technical field. Whether a particular term should be construed as such a "term of art" depends on the context in which that term is used. Such terms are to be construed in light of the context in which they are used in the present disclosure and as one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings and topic headings herein are provided for consistency with the suggestions under various patent regulations and practice, or otherwise to provide organizational cues. These headings shall not limit or characterize the embodiments set out in any claims that may issue from this disclosure. Specifically, a description of a technology in the "Background" is not to be construed as an admission that technology is prior art to any embodiments in this disclosure. Furthermore, any reference in this disclosure to "invention" in the singular should not be used to argue that there is only a single point of novelty in this disclosure. Multiple inventions may be set forth according to the limitations of the claims issuing from this disclosure, and such claims accordingly define the invention(s), and their equivalents, that are protected thereby. In all instances, the scope of such claims shall be considered on their own merits in light of this disclosure, but should not be constrained by the headings herein.

The invention claimed is:

1. A surgical system for performing an endoscopic retrograde cholangiopancreatography (ERCP) cannulation, the surgical system comprising:
  a main assembly, the main assembly including:
    a main body for inserting into a cavity of a patient;
    an inertial measurement unit (IMU) subsystem housed in the main body, the IMU subsystem configured to provide real-time IMU information, including real-time 3-dimensional position information of the main assembly, wherein the real-time 3-dimensional position information of the main assembly is generated by the IMU subsystem based on real-time orientation information and real-time acceleration information;
    an image capturing subsystem housed in the main body, the image capturing subsystem configured to capture real-time images; and
    a scope head assembly housed in the main body, the scope head assembly having a proximal end and a distal end, the scope head assembly configured to selectively extend the distal end of the scope head assembly outwardly from the main body, wherein at least a portion of the scope head assembly is configured to selectively bend in a plurality of directions; and
  a processor, the processor configured to:
    receive the real-time dimensional position information of the main assembly from the IMU subsystem;
    receive the real-time images from the image capturing subsystem;
    determine whether or not the received images include the distal end of the scope head assembly;
    responsive to a determination that the received images include the distal end of the scope head assembly:
      identify the distal end of the scope head assembly in the obtained images; and
      generate, based on the received real-time 3-dimensional position information of the main assembly, real-time 3-dimensional positions of the distal end of the scope head assembly;
    determine whether or not the received images include a cannulation target;
    responsive to a determination that the received images include the cannulation target:
      identify the cannulation target in the received images; and generate, based on the real-time 3-dimensional position information of the main assembly and the received images, real-time 3-dimensional positions of the cannulation target;

responsive to a determination that the received images include the distal end of the scope head assembly and the cannulation target:

predict, based on the 3-dimensional position of the distal end of the scope head assembly and the 3-dimensional position of the cannulation target, one or more real-time trajectory paths for the identified distal end of the scope head assembly to cannulate the identified cannulation target.

2. The surgical system of claim 1,
wherein the real-time images received from the image capturing subsystem includes real-time video images.

3. The surgical system of claim 1,
wherein the main assembly includes a duodenoscope.

4. The surgical system of claim 1,
wherein the scope head assembly includes a wire guided device and/or a catheter.

5. The surgical system of claim 1,
wherein the processor is further configured to:
generate, based on the real-time 3-dimensional positions of the identified distal end of the scope head assembly and the real-time 3-dimensional positions of the identified cannulation target, real-time depth information between the identified cannulation target and the identified distal end of the scope head assembly.

6. The surgical system of claim 1, further comprising:
a graphical display in communication with the processor and the main assembly;
wherein the processor is further configured to:
display, on the graphical display, the real-time images captured by the image capturing subsystem;
generate, in the real-time images that are displayed on the graphical display, a visible indicator for the identified cannulation target.

7. The surgical system of claim 6,
wherein the processor is further configured to:
generate, in the real-time images that are displayed on the graphical display, a visible indicator for the identified distal end of the scope head assembly.

8. The surgical system of claim 6, further comprising:
generating, in the real-time images that are displayed on the graphical display, a visible indicator for the one or more predicted real-time trajectory paths between the identified distal end of the scope head assembly and the identified cannulation target.

9. The surgical system of claim 1,
wherein the processor is further configured to:
adjust an initial position, orientation, and movement of the distal end of the scope head assembly based on the predicted trajectory paths.

* * * * *